United States Patent
Stuart et al.

(10) Patent No.: US 9,375,485 B2
(45) Date of Patent: Jun. 28, 2016

(54) USE OF TELOMERASE INHIBITORS FOR THE TREATMENT OF MYELOPROLIFERATIVE DISORDERS AND MYELOPROLIFERATIVE NEOPLASMS

(71) Applicant: Geron Corporation, Menlo Park, CA (US)

(72) Inventors: Monic J. Stuart, Hillsborough, CA (US); Stephen Kelsey, Palo Alto, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 13/841,711

(22) Filed: Mar. 15, 2013

(65) Prior Publication Data

US 2014/0163090 A1    Jun. 12, 2014

Related U.S. Application Data

(60) Provisional application No. 61/734,941, filed on Dec. 7, 2012.

(51) Int. Cl.
| | | |
|---|---|---|
| *A61K 47/48* | (2006.01) | |
| *A61K 49/04* | (2006.01) | |
| *B82Y 5/00* | (2011.01) | |

(52) U.S. Cl.
CPC ..... *A61K 47/48092* (2013.01); *A61K 47/48046* (2013.01); *A61K 49/0423* (2013.01); *B82Y 5/00* (2013.01)

(58) Field of Classification Search
USPC .................. 435/6, 91.1, 91.31, 455, 458, 6.1; 514/44, 1, 2; 536/23.1, 24.5; 424/9.1
See application file for complete search history.

(56) References Cited

U.S. PATENT DOCUMENTS

| | | | |
|---|---|---|---|
| 5,583,016 A | 12/1996 | Villeponteau et al. | |
| 5,656,638 A | 8/1997 | Gaeta et al. | |
| 5,695,932 A | 12/1997 | West et al. | |
| 5,760,062 A | 6/1998 | Gaeta et al. | |
| 5,767,278 A | 6/1998 | Gaeta et al. | |
| 5,770,613 A | 6/1998 | Gaeta et al. | |
| 5,840,490 A | 11/1998 | Bacchetti et al. | |
| 5,863,936 A | 1/1999 | Gaeta et al. | |
| 5,952,490 A | 9/1999 | Hanecak et al. | |
| 5,958,680 A | 9/1999 | Villeponteau et al. | |
| 6,261,836 B1 | 7/2001 | Cech et al. | |
| 6,331,399 B1 | 12/2001 | Monia et al. | |
| 6,368,789 B1 | 4/2002 | West et al. | |
| 6,444,650 B1 | 9/2002 | Cech et al. | |
| 6,548,298 B2 | 4/2003 | Villeponteau et al. | |
| 6,608,036 B1 | 8/2003 | Gryaznov et al. | |
| 7,067,497 B2 | 6/2006 | Hanecak et al. | |
| 7,485,717 B2 | 2/2009 | Gryaznov et al. | |
| 7,494,982 B2 | 2/2009 | Gryaznov et al. | |
| 7,563,618 B2 | 7/2009 | Gryaznov et al. | |
| 7,989,428 B2 | 8/2011 | Go et al. | |
| 7,998,938 B2 | 8/2011 | Moore et al. | |
| 8,153,604 B2 | 4/2012 | Deen et al. | |
| 8,440,635 B2 | 5/2013 | Gryaznov et al. | |
| 2005/0113325 A1 | 5/2005 | Gryaznov et al. | |
| 2005/0282893 A1 | 12/2005 | Au et al. | |
| 2006/0009636 A1 | 1/2006 | Gryaznov et al. | |
| 2006/0166221 A1 | 7/2006 | Bahou et al. | |
| 2007/0015723 A1 | 1/2007 | Hanecak et al. | |
| 2007/0224598 A1 | 9/2007 | Chang | |
| 2007/0270363 A1 | 11/2007 | Bennett et al. | |
| 2009/0162849 A1 | 6/2009 | Vainchenker et al. | |
| 2010/0104586 A1 | 4/2010 | Tressler et al. | |
| 2011/0263685 A1 | 10/2011 | Harley et al. | |
| 2013/0253042 A1* | 9/2013 | Gryaznov et al. ........... 514/44 R |
| 2014/0155465 A1 | 6/2014 | Bassett et al. | |
| 2014/0193518 A1* | 7/2014 | Sayeski et al. ............... 424/617 |
| 2014/0329890 A1* | 11/2014 | Gryaznov et al. ........... 514/44 R |
| 2015/0017119 A1* | 1/2015 | Fantl et al. .................. 424/85.1 |

FOREIGN PATENT DOCUMENTS

| | | |
|---|---|---|
| WO | 01/18015 | 3/2001 |
| WO | 02/077184 | 10/2002 |
| WO | 2004/029277 | 4/2004 |
| WO | 2005/023994 | 3/2005 |
| WO | 2006/113426 | 10/2006 |
| WO | 2008/054711 | 5/2008 |
| WO | 2008/112129 | 9/2008 |
| WO | 2010/045245 | 4/2010 |
| WO | WO 2011/098901 | 8/2011 |
| WO | WO 2013/059738 | 4/2013 |

(Continued)

OTHER PUBLICATIONS

Asai, A. et al., "A Novel Telomerase Template Antagonist (GRN163) as a Potential Anticancer Agent", Cancer Res. 63, 2003, pp. 3931-3939.

Baerlocher, G et al., "Imetelstat: A Novel Approach with Robust Hematologic and Molecular Responses in a Phase 2 study in Patients with Essential Thrombocythemia (ET) who are Refractory or Intolerant to Prior Therapy", Hematologica 98(s1) Abstract S112, 2012.

Baerlocher, G M. et al., "Imetelstat rapidly Induces and Maintains Substantial Hematologic and Molecular Responses in Patients with Essential Thrombocythemia (ET) who are Refractory or Intolerant to Prior Therapy:Preliminary Phase II Results", Blood (ASH Meeting Abstracts) vol. 120, No. 21, 2012, Abstract 179.

Brassat, et al., "Functional p53 is required for effective execution of telomerase inhibition in BCR-ABL-positive CML cells", Experimental Hematology 39(1), 2011, 66-76.

Brunold, C. et al., "Imetelstat, a Potent Telomerase Inhibitor, Inhibits the Spontaneous Growth of CFU-Meg In Vitro From Essential Thrombocythemia Patients but Not From Healthy Individuals", Blood (ASH Annual Meeting Abstr.) 118: Abstract 3843, 2011, 2 pages.

(Continued)

*Primary Examiner* — Jane Zara
(74) *Attorney, Agent, or Firm* — Glenn J. Foulds; Carol L. Francis; Bozicevic, Field & Francis LLP

(57) ABSTRACT

Provided herein are methods for reducing neoplastic progenitor cell proliferation and alleviating symptoms associated in individuals diagnosed with or thought to have Essential Thrombocythemia (ET). Also provided herein are methods for using telomerase inhibitors for maintaining blood platelet counts at relatively normal ranges in the blood of individuals diagnosed with or suspected of having ET.

53 Claims, 9 Drawing Sheets

(56) References Cited

FOREIGN PATENT DOCUMENTS

| WO | 2014/085632 | 6/2014 |
|---|---|---|
| WO | 2015/069758 | 5/2015 |

OTHER PUBLICATIONS

Drummond, M W. et al., "Dysregulated expression of the major telomerase components in leukemic stem cells", Leukemia, vol. 19, 2005, 381-389.

El-Daly, H et al., "Selective Cytotoxicity and telomere damage in leukemia cells using the telomerase inhibitor BIBR1532", Blood vol. 105, No. 4, 2005, 1742-1749.

Geron Corp, "Geron discontinues GRN1005 and Restructures to Focus on Imetelstat Development in Hematologic Malignancies and Solid Tumors with Short Telomeres", Press Release, 2012.

Geron Corp, "Geron Updates Imetelstat Development Strategy, Including Progress of Investigator-sponsored study in Myelofibrosis", Press Release, 2013.

Hanahan et al., "Hallmarks of Cancer: The Next Generation," Cell, 144, 2011, 646-674.

Harley, C et al., "Telomerase, Checkpoints and Cancer", Cancer Surv. 29, 1997, 263-284.

Hochreiter, A. et al., "Telomerase template antagonist GRN163L disrupts telomere maintenance, tumor growth, and metastasis of breast cancer", Clin. Cancer Res. 12(10), 2006, pp. 3184-3192.

Joseph, Immanual et al., "The Telomerase Inhibitor Imetelstat Depletes Cancer Stem Cells in Breast and Pancreatic Cancer Cell Lines", Cancer Research Online 70: 9494-9504, doi:10.1158/0008-5472.CAN-10-0233, 2010.

Kelland, Lloyd R. , "Overcoming the immortality of tumour cells by telomere and telomerase based cancer therapeutics", Eur. J Cancer, 41, 2005, 971-979.

Keller, G et al., "Telomeres and telomerase in chronic myeloid leukemia: impact for pathogenesis disease progression and targeted therapy", Hematological Oncology, vol. 27, No. 3, 2009, 123-129.

Kim, N. et al., "Specific association of human telomerase activity with immortal cells and cancer", Science 266, 1994, pp. 2011-2014.

Lee, J.-J. et al., "Telomere length shortening in non-Hodgkin's lymphoma patients undergoing chemotherapy", Ann. Hematol. 82, 2003, pp. 492-495.

Ly, Hinh et al., "Functional characterization of telomerase RNA variants found in patients with hematologic disorders", Blood, vol. 105, No. 6, 2005, 2332-2339.

Maritz, M F. et al., "Targeting telomerase in Hematologic malignancy", Future Oncology, vol. 6, No. 5, 2010, 769-789.

Pruzan, R. et al., "Allosteric inhibitors of telomerase: oligonucleotide N3'—>P5' phosphoramidates", Nucl. Acids Res. 30(2), 2002, pp. 559-568.

Puri, Neela et al., "Novel Therapeutics Targeting Telomerase and Telomeres", J. Cancer Sci. Ther., vol. 5, e127, doi:10.4172/1948-5956 1000e127, 2012.

Ratain, M. et al., "A phase I trial of GRN163L (GRN), a first-in-class telomere inhibitor, in advanced solid tumors", J. Clin. Oncol. 26, 2008, p. 3581.

Roth, A et al., "Imetelstat (GRN163L)—telomerase-based cancer therapy", Recent Results in Cancer Research, vol. 184, 2010, 221-234.

Roth, A et al., "Short Telomeres and High Telomerase Activity in T-cell Prolymphocytic Leukemia", Leukemia 21, 2007, 2456-2462.

Roth, A et al., "Telomerase is limiting the growth of acute myeloid leukemia cells", Leukemia, vol. 17, No. 12, Dec. 2003, 2410-2417.

Ruden, Maria et al., "Novel anticancer therapeutics targeting telomerase", Cancer Treatment Reviews, vol. 39, 2013, 444-456.

Ruella, Marco et al., "Telomere length in pH-negative chronic myeloproliferative neoplasms: it is reduced according to JAK2 V617F mutation allele burden and it is not affected by cytoreductive treatment with hydroxyurea", ASH Annual Meeting Abstracts 116, 2010, 1975.

Shaffer, Catherine , "Geron Hit Hard by Termination of Phase II Brain Cancer Trial", Bioworld Today vol. 23, No. 235, Dec. 5, 2012, 1, 4, 7.

Shay, J. et al., "A survey of telomerase activity in human cancer", Eur. J. Cancer 33, 1997, pp. 787-791.

Shea, R. et al., "Synthesis, hybridization properties and antiviral activity of lipid-oligodeoxynucleotide conjugates", Nucl. Acids Res. 18(13), 1990, pp. 3777-3783.

Shea-Herbert, B. et al., "Inhibition of human telomerase in immortal human cells leads to progressive telomere shortening and cell death", Proc. Natl. Acad. Sci. USA 96(25), 1999, pp. 14276-14281.

Shea-Herbert, B. et al., "Lipid modification of GRN163, an N3'-P5' thio-phosphoramidate oligonucleotide, enhance the potency of telomerase inhibition", Oncogene 24, 2005, pp. 5262-5268.

Shea-Herbert, B. et al., "Oligonucleotide N3'—>P5' phosphoramidates as efficient telomerase inhibitors", Oncogene 21, 2002, pp. 638-642.

Sumi, M et al., "A G-quadruplex interactive agent, telomestatin (SOT-095) induces telomere shortening with apoptosis and enhances chemosensitivity in acute myeloid leukemia", International Journal of Oncology, vol. 24, No. 6, Jun. 2004, 1481-1487.

Theophile, K. et al., "The expression levels of telomerase catalytic subunit hTERT and oncogenic MYC in essential thrombocythemia are affected by the molecular subtype," Ann Hematol. Apr. 2008;87(4):263-8. Epub Dec. 15, 2007.

Thompson, Patrick A. et al., "A Phase I Trial of Imetelstat in Children with Refractory or Recurrent Solid Tumors: A Children's Oncology Group Phase I Consortium Study (ADVL 1112)", Clinical Cancer Research; 1-7, 2013.

US National Institutes of Health, "Imetelstat Sodium in Treating Patients with Primary or Secondary Myelofibrosis", clinicaltrials.gov NCT01731951, 2012.

US National Institutes of Health, , "Open Label Study to Evaluate the Activity of Imetelstat in Patients with Essential Thrombocythemia or Polycythemia (ET/PV)", clinicaltrials.gov. NCT01243073, 2010.

Van Ziffle, Jessica A. et al., "Telomere length in subpopulations of human hematopoetic cells", Stem Cells 21, 2003, 654-660.

Wu, Kou-Juey et al., "Direct activation of Tert transcription by c-MYC", Nature Genetics 21, 1999, 220-224.

Yoon, S. Y. et al., "Telomere length shortening of peripheral blood mononuclear cells in solid-cancer patients undergoing standard-dose chemotherapy might be correlated with good treatment response and neutropenia severity", Acta Haematol. 118, 2007, pp. 30-37.

Wang, Eunice, S., et al., (2004) "Telomerase inhibition with an oligonucleotide telomerase template antagonist: in vitro and in vivo studies in multiple myeloma and lymphoma", Blood, 103(1):258-266.

Gryaznov, Sergei, M., (2012) "Oligonucleotide N3'-P5' Phosphoramidates and Thio-Phosphoramidates as Potential Therapeutic Agents", in Chemistry and Biology of Artificial Nucleic Acids, Egli and Herdewijn Eds., Wiley-VCH, 2012, pp. 61-77.

Gryaznov, Sergei, M., (1999) "Oligonucleotide N3'-P5' phosphoramidates as potential therapeutic agents", Biochimica et Biophysica Acta 1489,131-140.

Gryaznov, Sergei, M., (2010) "Oligonucleotide N3'-P5' Phosphoramidates and Thio-Phosphoramidates as Potential Therapeutic Agents", Chemistry & Biodiversity, 7:477-493.

Gryaznov, Sergei, M. and Letsinger, Robert, L. (1992) "Synthesis and properties of oligonucleotides containing aminodeoxythymidine units", Nucleic Acids Research, 20(13):3403-3409.

Gryaznov, Sergei, M., and Lloyd, David, H. (1993) "Modulation of oligonucleotide duplex and triplex stability via hydrophobic interactions", Nucleic Acids Research, 21(25):5909-5915.

Gryaznov, Sergei, M., et al. (1996) "Oligonucleotide N3'-P5' phosphoramidates as antisense agents", Nucleic Acids Research, 24(8):1508-1514.

Gryaznov, Sergei, M., and Winter, Holger (1998) "RNA mimetics: oligoribonucleotide N3'-P5' phosphoramidates", Nucleic Acids Research, 26(18):4160-4167.

Gryaznov, Sergei, M., et al. (2001) "Telomerase Inhibitors—Oligonucleotide Phosphoramidates as Potential Therapeutic Agents", Nucleosides, Nucleotides & Nucleic Acids, 20(4-7):401-410.

(56) References Cited

OTHER PUBLICATIONS

Pongracz, Krisztina, et al., (2003) "Novel Short Oligonucleotide Conjugates as Inhibitors of Human Telomerase", Nucleosides, Nucleotides & Nucleic Acids, 22(5-8):1627-1629.
Adams (1983) "Hindered dialkylamino nucleoside phosphite reagents in the synthesis of two DNA 51-mers" *J. Am. Chem. Soc.*; 105:661-663.
Asai et al. (2003) "A Novel Telomerase Template Antagonist (GRN163) as a Potential Anticancer Agent", Cancer Research, 63:3931-3939.
Barbui et al. (2009) "Perspectives on thrombosis in essential thrombocythemia and polycythemia vera: is leukocytosis a causative factor?" Blood; 114: 759-763.
Barosi et al. (2009) "Response criteria for essential thrombocythemia and polycythemia vera: result of a European LeukemiaNet consensus conference" *Blood*; 113(20):4829-4833.
Baxter et al. (2005) "Acquired mutation of the tyrosine kinase JAK2 in human myeloproliferative disorders" *Lancet*; 365:1054-1061.
Beaucage (1981) "Deoxynucleoside phosphoramidites—A new class of key intermediates for deoxypolynucleotide synthesis" *Tetra. Lett.*; 22:1859.
Beer et al. (2010) "How I treat essential thrombocythemia" *Blood*; 117(5):1472-1482.
Belousov (1997) "Sequence-specific targeting and covalent modification of human genomic DNA" *Nucleic Acids Res.*; 5(25):3440-3444.
Blackburn (1992) "Telomerases" *Ann. Rev. Biochem.*; 61:113-129.
Blommers (1994) "Effects of the Introduction of L-Nucleotides into DNA. Solution Structure of the Heterochiral Duplex d(G-C-G-(L)T-G-C-G).cntdot.d(C-G-C-A-C-G-C) Studied by NMR Spectroscopy" *Biochemistry*; 33:7886-7896.
Brown (1979) "Chemical synthesis and cloning of a tyrosine tRNA gene" *Meth. Enzymol.*; 68:109.
Carobbio et al. (2007) "Leukocytosis is a risk factor for thrombosis in essential thrombocythemia: interaction with treatment, standard risk factors, and Jak2 mutation status" *Blood*; 109(6):2310-2313.
Carruthers (1982) "Chemical Synthesis and Biological Studies on Mutated Gene-control Regions" *Cold Springs Harbor Symp. Quant. Biol.*; 47:411-418.
Chen et al. (2000) "Secondary Structure of Vertebrate Telomerase RNA" *Cell*; 100:503-514.
El-Kassar et al. (1997) "Clonality Analysis of Hematopoiesis in Essential Thrombocythemia: Advantages of Studying T Lymphocytes and Platelets" *Blood*; 89:128-134.
Fialkow (1981) "Evidence that essential thrombocythemia is a clonal disorder with origin in a multipotent stem cell" *Blood*; 58:916-919.
Frenkel (1995) "12-dimethylbenz[a]anthracene induces oxidative DNA modification in vivo" *Free Radic. Biol. Med.*; 19:373-380.
Geron Corp (2012) "Geron Corporation Reports Fourth Quarter and Annual 2012 Financial Results" *Press Release*.
Gnatenko et al. (2003) "Transcript profiling of human platelets using microarray and serial analysis of gene expression" *Blood*; 101:2285-2293.
Gryaznov et al. (2003) "Oligonucleotide N3' -> P5' Thiophosphoramidate Telomerase Template Antagonists as Potential Anticancer Agents" *Nucleosides, Nucleotides & Nucleic Acids*; 22(5-8):577-581.
Harley (1991) "Telomere loss: mitotic clock or genetic time bomb?" *Mutation Research*; 256:271-282.

James et al. (2005) "A unique clonal JAK2 mutation leading to constitutive signaling causes polycythaemia vera" *Nature*; 434:1144-1148.
Kim et al. (2001) "A low threshold level of expression of mutant-template telomerase RNA inhibits human tumor cell proliferation" *Proc. Natl. Acad. Sci. USA*; 98(14):7982-7987.
Kralovics et al. (2005) "A Gain-of-Function Mutation of JAK2 in Myeloproliferative Disorders" *N. Engl. J. Med.*; 352:1779-1790.
Kupihar et al. (2001) "Synthesis and Application of a Novel, Crystalline Phosphoramidite Monomer with Thiol Terminus, Suitable for the Synthes" *Bioorg. Med. Chem.*; 9:1241-1247.
Lebedeva et al. (2001) "Antisense Oligonucleotides: Promise and Reality" *Annual Review of Pharmacology and Toxicology*; 41:403-419.
Levine et al. (2005) "Activating mutation in the tyrosine kinase JAK2 in polycythemia vera, essential thrombocythemia, and myeloid metaplasia with myelofibrosis" *Cancer Cell*; 7:387-397.
Macejak et al. (1999) "Adenovirus-Mediated Expression of a Ribozyme to c-myb mRNA Inhibits Smooth Muscle Cell Proliferation and Neointima Formation In Vivo" *Journal of Virology*; 73(9):7745-7751.
Makishima et al. (2012) "Mutations in the spliceosome machinery, a novel and ubiquitous pathway in leukemogenesis" *Blood*; 119(14):3203-3210.
McCurdy et al. (1997) "An Improved Method for the Synthesis of N3'->P5' Phosphoramidate Oligonucleotides" *Tetrahedron Letters*; 38:207-210.
Mishra et al. (1995) "Improved leishmanicidal effect of phosphorotioate antisense oligonucleotides by LDL-mediated delivery" *Biochim. Et Biophys. Acta*; 1264:229-237.
Narang (1979) "[6] Improved phosphotriester method for the synthesis of gene fragments," *Meth. Enzymol.*; 68:90.
Nelson et al. (1997) "N3'->P5' Oligodeoxyribonucleotide Phosphoramidates: A New Method of Synthesis Based on a Phosphoramidite Amine-Exchange Reaction" *J. Org. Chem.*; 62:7278-7287.
Nimer (1999) "Essential Thrombocythemia: Another "Heterogeneous Disease" Better Understood?" *Blood*; 93:415-416.
Papaemmanuil et al. (2011) "Somatic SF3B1 Mutation in Myelodysplasia with Ring Sideroblasts" N Engl J Med. 365(15):1384-1395.
Pascolo et al. (2002) "Mechanism of Human Telomerase Inhibition by BIBR1532, a Synthetic, Non-nucleosidic Drug Candidate" *J. Biol. Chem.*; 277(18):15566-15572.
Pongracz and Gryaznov (1999) "Oligonucleotide N3'->P5' thiophosphoramidates: synthesis and properties" *Tetrahedron Letters*; 49:7661-7664.
Rump et al. (1995) "Preparation of Conjugates of Oligodeoxynucleotides and Lipid Structures and Their Interaction with Low-Density Lipoprotein" *Bioconj. Chem.*; 9:341-349.
Uhlmann and Peyman (1990) "Antisense oligonucleotides: a new therapeutic principle" *Chemical Reviews*; 90:543-584.
Ward and Autexier (2005) "Pharmacological Telomerase Inhibition Can Sensitize Drug-Resistant and Drug-Sensitive Cells to Chemotherapeutic Treatment" *Mol. Pharmacol.*; 68:779-786.
Zeng et al. (2003) "MicroRNAs and small interfering RNAs can inhibit mRNA expression by similar mechanisms" *PNAS*; 100(17):9779-9784.
Ziakas (2008) "Effect of JAK2 V617F On Thrombotic Risk In Patients With Essential Thrombocythemia: Measuring The Uncertain" *Haematologica*; 93: 1412-1414.

* cited by examiner

A

A

B

```
                        SEQUENCE LISTING

<160> NUMBER OF SEQ ID NOS: 22

<210> SEQ ID NO 1
<211> LENGTH: 554
<212> TYPE: RNA
<213> ORGANISM: Homo sapiens

<400> SEQUENCE: 1
ggguugcgga ggugggccu gggagggug guggccauuu uuugucuaac ccuaacugag      60
aagggcguag cgccgugcu uuugcuccc gcgcgcuguu uuucucgcug acuuucagcg     120
ggcggaaaag ccucggccug ccgccuucca ccguucauuc uagagcaaac aaaaaauguc   180
agcugcuggc ccguucgccu cccggggacc ugcggcgggu cgccugccca gcccccgaac   240
cccgccugga gccgcggucg gccggggcu ucuccggagg cacccacugc caccgcgaag    300
aguugggcuc ugucagccgc gggucucucg ggggcgaggg cgagguucac cguuucaggc   360
cgcaggaaga ggaacggagc gaguccgcc gcggcgcgau ucccugagcu gugggacgug    420
cacccaggac ucggcucaca caugcaguuc gcuuuccugu uggugggggg aacgccgauc   480
gugcgcaucc gucacccuc gccggcagug ggggcuugug aacccccaaa ccugacugac    540
ugggccagug ugcu                                                     554

<210> SEQ ID NO 2
<211> LENGTH: 20
<212> TYPE: DNA
<213> ORGANISM: Homo sapiens

<400> SEQUENCE: 2
acattttttg tttgctctag                                                20

<210> SEQ ID NO 3
<211> LENGTH: 30
<212> TYPE: DNA
<213> ORGANISM: Homo sapiens

<400> SEQUENCE: 3
gctctagaat gaacggtgga aggcggcagg                                     30

<210> SEQ ID NO 4
<211> LENGTH: 14
<212> TYPE: DNA
<213> ORGANISM: Homo sapiens

<400> SEQUENCE: 4
gtggaggcgg cagg                                                      14

<210> SEQ ID NO 5
```

```
<211> LENGTH: 13
<212> TYPE: DNA
<213> ORGANISM: Homo sapiens

<400> SEQUENCE: 5
ggaaggcggc agg                                                    13

<210> SEQ ID NO 6
<211> LENGTH: 13
<212> TYPE: DNA
<213> ORGANISM: Homo sapiens

<400> SEQUENCE: 6
gtggaaggcg gca                                                    13

<210> SEQ ID NO 7
<211> LENGTH: 11
<212> TYPE: DNA
<213> ORGANISM: Homo sapiens

<400> SEQUENCE: 7
gtggaaggcg g                                                      11

<210> SEQ ID NO 8
<211> LENGTH: 13
<212> TYPE: DNA
<213> ORGANISM: Homo sapiens

<400> SEQUENCE: 8
cggtggaagg cgg                                                    13

<210> SEQ ID NO 9
<211> LENGTH: 13
<212> TYPE: DNA
<213> ORGANISM: Homo sapiens

<400> SEQUENCE: 9
acggtggaag gcg                                                    13

<210> SEQ ID NO 10
<211> LENGTH: 16
<212> TYPE: DNA
<213> ORGANISM: Homo sapiens

<400> SEQUENCE: 10
aacggtggaa ggcggc                                                 16

<210> SEQ ID NO 11
<211> LENGTH: 18
<212> TYPE: DNA
<213> ORGANISM: Homo sapiens

<400> SEQUENCE: 11
atgaacggtg gaaggcgg                                               18

<210> SEQ ID NO 12
<211> LENGTH: 13
<212> TYPE: DNA
<213> ORGANISM: Homo sapiens

<400> SEQUENCE: 12
tagggttaga caa                                                    13
```

```
<210> SEQ ID NO 13
<211> LENGTH: 13
<212> TYPE: DNA
<213> ORGANISM: Homo sapiens

<400> SEQUENCE: 13
cagttagggt tag                                                        13

<210> SEQ ID NO 14
<211> LENGTH: 12
<212> TYPE: DNA
<213> ORGANISM: Homo sapiens

<400> SEQUENCE: 14
tagggttaga ca                                                         12

<210> SEQ ID NO 15
<211> LENGTH: 11
<212> TYPE: DNA
<213> ORGANISM: Homo sapiens

<400> SEQUENCE: 15
tagggttaga c                                                          11

<210> SEQ ID NO 16
<211> LENGTH: 11
<212> TYPE: DNA
<213> ORGANISM: Homo sapiens

<400> SEQUENCE: 16
gttagggtta g                                                          11

<210> SEQ ID NO 17
<211> LENGTH: 13
<212> TYPE: DNA
<213> ORGANISM: Homo sapiens

<400> SEQUENCE: 17
gttagggtta gac                                                        13

<210> SEQ ID NO 18
<211> LENGTH: 15
<212> TYPE: DNA
<213> ORGANISM: Homo sapiens

<400> SEQUENCE: 18
gttagggtta gacaa                                                      15

<210> SEQ ID NO 19
<211> LENGTH: 12
<212> TYPE: DNA
<213> ORGANISM: Homo sapiens

<400> SEQUENCE: 19
cccttctcag tt                                                         12

<210> SEQ ID NO 20
<211> LENGTH: 12
<212> TYPE: DNA
<213> ORGANISM: Homo sapiens

<400> SEQUENCE: 20
cgcccttctc ag                                                         12
```

```
<210> SEQ ID NO 21
<211> LENGTH: 11
<212> TYPE: RNA
<213> ORGANISM: Artificial sequence
<220> FEATURE:
<223> OTHER INFORMATION: hTR template inhibitor

<400> SEQUENCE: 21
cuaacccuaa c                                                              11

<210> SEQ ID NO 22
<211> LENGTH: 13
<212> TYPE: DNA
<213> ORGANISM: Artificial sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: t is conjugated to a palmitoyl amide through an
      aminoglycerol linker to the 5' thiophosphate group of the
      oligonucleotide

<400> SEQUENCE: 22
tagggttaga caa                                                            13
```

US 9,375,485 B2

USE OF TELOMERASE INHIBITORS FOR THE TREATMENT OF MYELOPROLIFERATIVE DISORDERS AND MYELOPROLIFERATIVE NEOPLASMS

CROSS-REFERENCE TO RELATED APPLICATIONS

This application claims priority to U.S. Provisional Patent Application No. 61/734,941, filed Dec. 7, 2012, the disclosure of which is hereby incorporated by reference herein in its entirety.

INCORPORATION BY REFERENCE

The content of the following submission on ASCII text file is incorporated herein by reference in its entirety: a computer readable form (CRF) of the Sequence Listing (file name: 182-003 seqlist.txt, date created: Jul. 14, 2015, size: 4,629 bytes).

FIELD OF THE INVENTION

This invention relates to methods for using telomerase inhibitor compounds to treat or prevent symptoms associated with myeloproliferative disorders or neoplasms such as Essential Thrombocythemia (ET).

BACKGROUND

Hematologic malignancies are forms of cancer that begin in the cells of blood-forming tissue, such as the bone marrow, or in the cells of the immune system. Examples of hematologic cancer are acute and chronic leukemias, lymphomas, multiple myeloma and myelodysplastic syndromes.

Myeloproliferative neoplasms, or MPNs, are hematologic neoplasms that arise from neoplastic hematopoietic myeloid progenitor cells in the bone marrow, such as the precursor cells of red cells, platelets and granulocytes. Proliferation of neoplastic progenitor cells leads to an overproduction of any combination of white cells, red cells and/or platelets, depending on the disease. These overproduced cells may also be abnormal, leading to additional clinical complications. There are various types of chronic myeloproliferative disorders. Included in the MPN disease spectrum are Essential Thrombocythemia (ET), Polycythemia vera (PV), ChronicMyelogenous Leukemia (CML), myelofibrosis (MF), chronic neutrophilic leukemia, chronic eosinophilic leukemia and acute myelogenous leukemia (AML). A myelodysplastic syndrome (MDS) is a group of symptoms that includes cancer of the blood and bone marrow. Myelodysplastic syndromes (MDS) includes diseases such as, refractory anemia, refractory anemia with excess blasts, refractory cytopenia with multilineage dysplasia, refractory cytopenia with unilineage dysplasia, and chronic myelomonocytic leukemia (CMML).

Essential Thrombocythemia

Circulating blood platelets are anucleate, although they retain small amounts of megakaryocyte-derived mRNAs and a fully functional protein biosynthetic capacity (Gnatenko et al., Blood 101, 2285-2293 (2003)). Essential Thrombocythemia (ET) is a myeloproliferative disorder subtype, characterized by increased neoplastic proliferation of megakaryocytes, elevated numbers of circulating platelets, and considerable thrombohemorrhagic events, not infrequently neurological (Nimer, Blood 93, 415-416 (1999)). ET is seen with equal frequency in males and females, although an additional female incidence peak at age 30 may explain the apparent higher disease prevalence in females after this age. The molecular basis of ET remains to be established, although historically it has been considered a "clonal" disorder (El-Kassar et al., Blood 89, 128 (1997); "Evidence that ET is a clonal disorder with origin in a multipotent stem cell" P J Fialkow, Blood 1981 58: 916-919). Other than the exaggerated platelet volume evident in subsets of ET platelets, the cells remain morphologically indistinguishable from their normal counterparts. No functional or diagnostic test is currently available for ET, and it remains to be diagnosed by exclusion of other potential hematological disorders Incidence estimates of 2-3 cases per 100,000 per year are consistent with other types of leukemia, but prevalence rates are at least ten times higher due to the low mortality rates associated with ET.

Current therapies for ET focus primarily on prevention of thrombotic/hemorrhagic occurrence and involve non-specific reduction of blood platelet levels. However, none of these existing therapies focus specifically on the neoplastic progenitor cells driving the malignancy responsible for the disease state. For example, treatment of ET with cytotoxic chemotherapy debulks neoplastic cells while leaving residual progenitor cells in place. This results in new neoplastic cells arising from the progenitor cells and continuation of the disease state. Additionally, many individuals with ET develop resistance to front-line treatments such as hydroxyurea or discontinue use of these drugs altogether due to adverse side effects.

Polycythemia Vera

Patients with Polycythemia Vera (PV) have marked increases of red blood cell production. Treatment is directed at reducing the excessive numbers of red blood cells. PV can develop a phase late in their course that resembles primary myelofibrosis with cytopenias and marrow hypoplasia and fibrosis. The Janus Kinase 2 gene (JAK2) gene mutation on chromosome 9 which causes increased proliferation and survival of hematopoietic precursors in vitro has been identified in most patients with PV. Patients with PV have an increased risk of cardiovascular and thrombotic events and transformation to acute myelogenous leukemia or primary myelofibrosis. The treatment for PV includes intermittent chronic phlebotomy to maintain the hematocrit below 45% in men and 40% in women. Other possible treatments includes hydroxyurea, interferon-alpha, and low-dose aspirin.

Myelofibrosis

Myelofibrosis or MF, or primary myelofibrosis is a myeloproliferative neoplasm in the same spectrum of diseases as ET. Patients with MF often carry the JAK2 V617F mutation in their bone marrow. Occasionally ET evolves into MF. JAK2 inhibition is currently considered a standard of care for MF in countries where ruxolitinib (Jakafi®), a janus kinase inhibitor, is approved. There is no evidence that JAK2 inhibitors, such as Jakafi®, selectively inhibit proliferation of the leukemic clone responsible for the disease and thus, they may not be "disease modifying".

Acute Myelogenous Leukemia

Acute Myelogenous Leukemia (AML) is a cancer of the myeloid line of blood cells. AML is the most common acute leukemia affecting adults. Patients with AML have a rapid growth of abnormal white blood cells that accumulate in the bone marrow and interfere with the production of normal blood cells. Replacement of normal bone marrow with leukemic cells causes a drop in red blood cells, platelets, and normal white blood cells. The symptoms of AML include fatigue, shortness of breath, easy bruising and bleeding, and increased risk of infection. As an acute leukemia, AML progresses rapidly and is typically fatal within weeks or months if left untreated. The standard of care for AML is treatment with chemotherapy aimed at inducing a remission; patients may go on to receive a hematopoietic stem cell transplant.

Myelodysplastic Syndrome

A myelodysplastic syndrome (MDS) is a group of symptoms that includes cancer of the blood and bone marrow. Myelodysplastic syndromes (MDS) includes diseases such as, refractory anemia, refractory anemia with excess blasts, refractory cytopenia with multilineage dysplasia, refractory cytopenia with unilineage dysplasia, and chronic myelomonocytic leukemia. The immature blood stem cells (blasts) do not become healthy red blood cells, white blood cells or platelets. The blast die in the bone marrow or soon after they travel to the blood. This leaves less room for healthy white cells, red cells and/or platelets to form in the bone marrow.

The myelodysplastic syndromes (MDS) are a collection of hematological medical conditions that involve ineffective production of the myeloid class of blood cells. Patients with MDS often develop severe anemia and require frequent blood transfusions. Bleeding and risk of infections also occur due to low or dysfunctional platelets and neutrophils, respectively. In some cases the disease worsens and the patient develops cytopenias (low blood counts) caused by progressive bone marrow failure. In some cases the disease transforms into acute myelogenous leukemia (AML). If the overall percentage of bone marrow myeloblasts rises over a particular cutoff (20% for WHO and 30% for FAB), then transformation to acute myelogenous leukemia (AML) is said to have occurred.

What is needed, therefore, are new treatments for myelodysplastic proliferative disorders or neoplasm such as ET, PV, MF, CML and AML, and for myelodysplastic syndrome which target the neoplastic progenitor cells responsible for the disease's malignant phenotype, particularly in individuals who are resistant to or experience adverse events as a result of taking commonly prescribed front-line therapies for this disorder.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY OF THE INVENTION

The invention provided herein discloses, inter alia, methods for using telomerase inhibitor compounds to treat and alleviate symptoms associated with myeloproliferative neoplasms such as Essential Thrombocythemia (ET), Polycythemia Vera (PV), Myelofibrosis (MF), and Acute Myelogenous Leukemia (AML) by targeting the neoplastic progenitor cells characteristic of these diseases. The invention provided herein also discloses, inter alia, methods for using telomerase inhibitor compounds to treat and alleviate symptoms associated with myelodysplastic syndromes (MDS) such as, for example, refractory anemia, refractory anemia with excess blasts, refractory cytopenia with multilineage dysplasia, refractory cytopenia with unilineage dysplasia, and chronic myelomonocytic leukemia by targeting the neoplastic progenitor cells responsible for producing the abnormally high numbers of cells characteristic of these diseases.

Accordingly, in one aspect, provided herein are methods for alleviating at least one symptom associated with myeloproliferative neoplasms in an individual in need thereof, the method comprising: administering a clinically effective amount of a telomerase inhibitor to the individual, wherein administration of the telomerase inhibitor alleviates at least one symptom associated with myeloproliferative neoplasms. In some embodiments, the symptom comprises headache, dizziness or lightheadedness, chest pain, weakness, fainting, vision changes, numbness or tingling of extremities, redness, throbbing or burning pain in extremities (erythromelalgia), enlarged spleen, nosebleeds, bruising, bleeding from mouth or gums, bloody stool, or stroke. In some embodiments the myeloproliferative neoplasms are, for example, Essential Thrombocythemia (ET), Polycythemia Vera (PV), Myelofibrosis (MF), and Acute Myelogenous Leukemia (AML). In some embodiments of any of the embodiments herein, the telomerase inhibitor comprises an oligonucleotide. In some embodiments, the oligonucleotide is complementary to the RNA component of telomerase. In some embodiments, the oligonucleotide is 10-20 base pairs in length. In some embodiments, the oligonucleotide comprises the sequence TAGGGTTAGACAA (SEQ ID NO:12). In some embodiments of any of the embodiments herein, the oligonucleotide comprises at least one N3'→P5' thiophosphoramidate internucleoside linkage. In some embodiments of any of the embodiments herein, oligonucleotide comprises N3'→P5' thiophosphoramidate internucleoside linkages. In some embodiments of any of the embodiments herein, the oligonucleotide further comprises a lipid moiety linked to the 5' and/or 3' end of the oligonucleotide. In some embodiments of any of the embodiments herein, the lipid moiety is linked to the 5' and/or 3' end of the oligonucleotide via a linker. In some embodiments, the linker is a glycerol or aminoglycerol linker. In some embodiments of any of the embodiments herein, the lipid moiety is a palmitoyl (C16) moiety. In some embodiments of any of the embodiments herein, the telomerase inhibitor is imetelstat. In some embodiments of any of the embodiments herein, the telomerase inhibitor is administered with a pharmaceutically acceptable excipient. In some embodiments of any of the embodiments herein, the telomerase inhibitor is formulated for oral, intravenous, subcutaneous, intramuscular, topical, intraperitoneal, intranasal, inhalation, or intraocular administration. In some embodiments of any of the embodiments herein, administration of the therapeutically effective amount of the telomerase inhibitor comprises contacting one or more neoplastic progenitor cells with the telomerase inhibitor. In some embodiments of any of the embodiments herein, the effective amount of a telomerase inhibitor is 7.5 mg/kg to 9.3 mg/kg. In some embodiments of any of the embodiments herein, the effective amount of a telomerase inhibitor is 9.5 mg/kg to 11.7 mg/kg. In some embodiments of any of the embodiments herein, administration of the telomerase inhibitor does not inhibit cytokine-dependent megakaryocyte growth. In some embodiments of any of the embodiments herein, the individual carries a V617F gain of function mutation in the Janus kinase 2 (JAK2) gene. In some embodiments, administration of the telomerase inhibitor decreases the percentage of JAK2 V617F allelic burden in the individual. In some embodiments of any of the embodiments herein, administration of the telomerase inhibitor inhibits cytokine-independent megakaryocyte growth. In some embodiments of any of the embodiments herein, administration of the telomerase inhibitor inhibits CFU-mega. In some embodiments, inhibition of CFU-Mega is independent of reduction in JAK2 allelic burden. In some embodiments, the individual is resistant or intolerant to a prior non-telomerase inhibitor-based therapy. In some embodiments, the individual is a human.

Accordingly, in one aspect, provided herein are methods for alleviating at least one symptom associated with essential thrombocythemia in an individual in need thereof, the method comprising: administering a clinically effective amount of a telomerase inhibitor to the individual, wherein administration of the telomerase inhibitor alleviates at least one symptom associated with essential thrombocythemia. In some embodiments, the symptom comprises headache, dizziness or lightheadedness, chest pain, weakness, fainting, vision changes, numbness or tingling of extremities, redness, throbbing or burning pain in extremities (erythromelalgia), enlarged spleen, nosebleeds, bruising, bleeding from mouth or gums, bloody stool, or stroke. In some embodiments of any of the embodiments herein, the telomerase inhibitor comprises an oligonucleotide. In some embodiments, the oligonucleotide is complementary to the RNA component of telomerase. In some embodiments, the oligonucleotide is 10-20 base pairs in length. In some embodiments, the oligonucleotide comprises the sequence TAGGGTTAGACAA (SEQ ID NO:12). In some embodiments of any of the embodiments herein, the oligonucleotide comprises at least one N3'→P5' thiophosphoramidate internucleoside linkage. In some embodiments of any of the embodiments herein, oligonucleotide comprises N3'→P5' thiophosphoramidate internucleoside linkages. In some embodiments of any of the embodiments herein, the oligonucleotide further comprises a lipid moiety linked to the 5' and/or 3' end of the oligonucleotide. In some embodiments of any of the embodiments herein, the lipid moiety is linked to the 5' and/or 3' end of the oligonucleotide via a linker. In some embodiments, the linker is a glycerol or aminoglycerol linker. In some embodiments of any of the embodiments herein, the lipid moiety is a palmitoyl (C16) moiety. In some embodiments of any of the embodiments herein, the telomerase inhibitor is imetelstat. In some embodiments of any of the embodiments herein, the telomerase inhibitor is administered with a pharmaceutically acceptable excipient. In some embodiments of any of the embodiments herein, the telomerase inhibitor is formulated for oral, intravenous, subcutaneous, intramuscular, topical, intraperitoneal, intranasal, inhalation, or intraocular administration. In some embodiments of any of the embodiments herein, administration of the therapeutically effective amount of the telomerase inhibitor comprises contacting one or more neoplastic progenitor cells with the telomerase inhibitor. In some embodiments of any of the embodiments herein, the effective amount of a telomerase inhibitor is 7.5 mg/kg to 9.3 mg/kg. In some embodiments of any of the embodiments herein, the effective amount of a telomerase inhibitor is 9.5 mg/kg to 11.7 mg/kg. In some embodiments of any of the embodiments herein, administration of the telomerase inhibitor does not inhibit cytokine-dependent megakaryocyte growth. In some embodiments of any of the embodiments herein, the individual carries a V617F gain of function mutation in the Janus kinase 2 (JAK2) gene. In some embodiments, administration of the telomerase inhibitor decreases the percentage of JAK2 V617F allelic burden in the individual. In some embodiments of any of the embodiments herein, administration of the telomerase inhibitor inhibits cytokine-independent megakaryocyte growth. In some embodiments of any of the embodiments herein, administration of the telomerase inhibitor inhibits CFU-mega. In some embodiments, inhibition of CFU-Mega is independent of reduction in JAK2 allelic burden. In some embodiments, the individual is resistant or intolerant to a prior non-telomerase inhibitor-based therapy. In some embodiments, the prior non-telomerase inhibitor-based therapy is hydroxyurea, anagrelide, or Interferon α-2B. In some embodiments, the individual is a human.

In another aspect, provided herein are methods for reducing neoplastic progenitor cell proliferation in an individual diagnosed with or suspected of having myeloproliferative neoplasms or myelodysplastic syndrome, the method comprising: administering a clinically effective amount of a telomerase inhibitor to the individual, wherein administration of the telomerase inhibitor reduces neoplastic progenitor cell proliferation in the individual. In some embodiments the myeloproliferative neoplasms are, for example, Essential Thrombocythemia (ET), Polycythemia Vera (PV), Myelofibrosis (MF), and Acute Myelogenous Leukemia (AML). In some embodiments, for ET reduced neoplastic progenitor cell proliferation results in platelet counts of less than about $600 \times 10^3/\mu L$ in the blood of the individual. In some embodiments, reduced neoplastic progenitor cell proliferation results in platelet counts of less than about $400 \times 10^3/\mu L$ in the blood of the individual. In some embodiments of any of the embodiment herein, the individual does not experience a thromboembolic event. In some embodiments of any of the embodiment herein, reduced neoplastic cell proliferation resulting in platelet counts of less than about $400 \times 10^3/\mu L$ in the blood of the individual occurs within 2 months or less following initiation of telomerase inhibitor administration. In some embodiments of any of the embodiment herein, reduced neoplastic cell proliferation resulting in platelet counts of less than about $400 \times 10^3/\mu L$ in the blood of the individual occurs within 1 month or less following initiation of telomerase inhibitor administration. In some embodiments, the individual is resistant or intolerant to a prior non-telomerase inhibitor-based therapy. In some embodiments, such as for MF, reduced neoplastic progenitor cell proliferation results in platelet counts of greater than about $100 \times 10^9/L$ in the blood of the individual. In some embodiments, such as for MF, reduced neoplastic progenitor cell proliferation results in modified hemoglobin level of at least 90 g/L, or 100 g/L or 110 g/L or 120 g/L. In some embodiments, such as for MF, reduced neoplastic progenitor cell proliferation results in modified absolute neutrophil count of at least $1.0 \times 10^9/L$ or at least $2.0 \times 10^9/L$. In some embodiments of any of the embodiments herein, the telomerase inhibitor comprises an oligonucleotide. In some embodiments, the oligonucleotide is complementary to the RNA component of telomerase. In some embodiments, the oligonucleotide is 10-20 base pairs in length. In some embodiments, the oligonucleotide comprises the sequence TAGGGTTAGACAA (SEQ ID NO:12). In some embodiments of any of the embodiments herein, the oligonucleotide comprises at least one N3'→P5' thiophosphoramidate internucleoside linkage. In some embodiments of any of the embodiments herein, oligonucleotide comprises N3'→P5' thiophosphoramidate internucleoside linkages. In some embodiments of any of the embodiments herein, the oligonucleotide further comprises a lipid moiety linked to the 5' and/or 3' end of the oligonucleotide. In some embodiments of any of the embodiments herein, the lipid moiety is linked to the 5' and/or 3' end of the oligonucleotide via a linker. In some embodiments, the linker is a glycerol or aminoglycerol linker. In some embodiments of any of the embodiments herein, the lipid moiety is a palmitoyl (C16) moiety. In some embodiments of any of the embodiments herein, the telomerase inhibitor is imetelstat. In some embodiments of any of the embodiments herein, the telomerase inhibitor is administered with a pharmaceutically acceptable excipient. In some embodiments of any of the embodiments herein, the telomerase inhibitor is formulated for oral, intravenous, subcutaneous, intramuscular, topical, intraperitoneal, intranasal, inhalation, or intraocular administration. In some embodiments of any of the embodiments herein, administration of the therapeutically effective amount of the telomerase inhibitor comprises contacting one or more neoplastic progenitor cells with the telomerase inhibitor. In some embodiments of any of the embodiments herein, the effective amount of a telomerase inhibitor is 7.5 mg/kg to 9.3 mg/kg. In some embodiments of any of the embodiments herein, the effective amount of a telomerase inhibitor is 9.5 mg/kg to 11.7 mg/kg. In some embodiments of any of the embodiments herein, administration of the telomerase inhibitor does not inhibit cytokine-dependent megakaryocyte growth. In some embodiments of any of the embodiments herein, the individual carries a V617F gain of function mutation in the Janus kinase 2 (JAK2) gene. In some embodiments, administration of the telomerase inhibitor decreases the percentage of JAK2 V617F allelic burden in the individual. In some embodiments of any of the embodiments herein, administration of the telomerase inhibitor inhibits cytokine-independent megakaryocyte growth. In some embodiments of any of the embodiments herein, administration of the telomerase inhibitor inhibits CFU-mega. In some embodiments, inhibition of CFU-Mega is independent of reduction in JAK2 allelic burden. In some embodiments, the individual is a human.

In another aspect, provided herein are methods for reducing neoplastic progenitor cell proliferation in an individual diagnosed with or suspected of having essential thrombocythemia, the method comprising: administering a clinically effective amount of a telomerase inhibitor to the individual, wherein administration of the telomerase inhibitor reduces neoplastic progenitor cell proliferation in the individual. In some embodiments, reduced neoplastic progenitor cell proliferation results in platelet counts of less than about 600×$10^3$/μL in the blood of the individual. In some embodiments, reduced neoplastic progenitor cell proliferation results in platelet counts of less than about 400×$10^3$/μL in the blood of the individual. In some embodiments of any of the embodiment herein, the individual does not experience a thromboembolic event. In some embodiments of any of the embodiment herein, reduced neoplastic cell proliferation resulting in platelet counts of less than about 400×$10^3$/μL in the blood of the individual occurs within 2 months or less following initiation of telomerase inhibitor administration. In some embodiments of any of the embodiment herein, reduced neoplastic cell proliferation resulting in platelet counts of less than about 400×$10^3$/μL in the blood of the individual occurs within 1 month or less following initiation of telomerase inhibitor administration. In some embodiments, the individual is resistant or intolerant to a prior non-telomerase inhibitor-based therapy. In some embodiments, the prior non-telomerase inhibitor-based therapy is hydroxyurea, anagrelide, or Interferon α-2B. In some embodiments of any of the embodiments herein, the telomerase inhibitor comprises an oligonucleotide. In some embodiments, the oligonucleotide is complementary to the RNA component of telomerase. In some embodiments, the oligonucleotide is 10-20 base pairs in length. In some embodiments, the oligonucleotide comprises the sequence TAGGGTTAGACAA (SEQ ID NO:12). In some embodiments of any of the embodiments herein, the oligonucleotide comprises at least one N3'→P5' thiophosphoramidate internucleoside linkage. In some embodiments of any of the embodiments herein, oligonucleotide comprises N3'→P5' thiophosphoramidate internucleoside linkages. In some embodiments of any of the embodiments herein, the oligonucleotide further comprises a lipid moiety linked to the 5' and/or 3' end of the oligonucleotide. In some embodiments of any of the embodiments herein, the lipid moiety is linked to the 5' and/or 3' end of the oligonucleotide via a linker. In some embodiments, the linker is a glycerol or aminoglycerol linker. In some embodiments of any of the embodiments herein, the lipid moiety is a palmitoyl (C16) moiety. In some embodiments of any of the embodiments herein, the telomerase inhibitor is imetelstat. In some embodiments of any of the embodiments herein, the telomerase inhibitor is administered with a pharmaceutically acceptable excipient. In some embodiments of any of the embodiments herein, the telomerase inhibitor is formulated for oral, intravenous, subcutaneous, intramuscular, topical, intraperitoneal, intranasal, inhalation, or intraocular administration. In some embodiments of any of the embodiments herein, administration of the therapeutically effective amount of the telomerase inhibitor comprises contacting one or more neoplastic progenitor cells with the telomerase inhibitor. In some embodiments of any of the embodiments herein, the effective amount of a telomerase inhibitor is 7.5 mg/kg to 9.3 mg/kg. In some embodiments of any of the embodiments herein, the effective amount of a telomerase inhibitor is 9.5 mg/kg to 11.7 mg/kg. In some embodiments of any of the embodiments herein, administration of the telomerase inhibitor does not inhibit cytokine-dependent megakaryocyte growth. In some embodiments of any of the embodiments herein, the individual carries a V617F gain of function mutation in the Janus kinase 2 (JAK2) gene. In some embodiments, administration of the telomerase inhibitor decreases the percentage of JAK2 V617F allelic burden in the individual. In some embodiments of any of the embodiments herein, administration of the telomerase inhibitor inhibits cytokine-independent megakaryocyte growth. In some embodiments of any of the embodiments herein, administration of the telomerase inhibitor inhibits CFU-mega. In some embodiments, inhibition of CFU-Mega is independent of reduction in JAK2 allelic burden. In some embodiments, the individual is a human.

In another aspect, provided herein are methods for maintaining blood platelet counts of less than about 400×$10^3$/μL in the blood of an individual diagnosed with or suspected of having essential thrombocythemia, the method comprising: administering a clinically effective amount of a telomerase inhibitor to the individual, wherein administration of the telomerase inhibitor maintains blood platelet counts of less than about 400×$10^3$/μL in the individual. In some aspects, the telomerase inhibitor is administered no more than once every two weeks. In other aspects, the telomerase inhibitor is administered to maintain blood platelet counts of between about 150×$10^3$/μL to about 400×$10^3$/μL in the blood of an individual. In some embodiments of any of the embodiments herein, the telomerase inhibitor comprises an oligonucleotide. In some embodiments, the oligonucleotide is complementary to the RNA component of telomerase. In some embodiments, the oligonucleotide is 10-20 base pairs in length. In some embodiments, the oligonucleotide comprises the sequence TAGGGTTAGACAA (SEQ ID NO:12). In some embodiments of any of the embodiments herein, the oligonucleotide comprises at least one N3'→P5' thiophosphoramidate internucleoside linkage. In some embodiments of any of the embodiments herein, oligonucleotide comprises N3'→P5' thiophosphoramidate internucleoside linkages. In some embodiments of any of the embodiments herein, the oligonucleotide further comprises a lipid moiety linked to the 5' and/or 3' end of the oligonucleotide. In some embodiments of any of the embodiments herein, the lipid moiety is linked to the 5' and/or 3' end of the oligonucleotide via a linker. In some embodiments, the linker is a glycerol or aminoglycerol linker. In some embodiments of any of the embodiments herein, the lipid moiety is a palmitoyl (C16) moiety. In some embodiments of any of the embodiments herein, the telomerase inhibitor is imetelstat. In some embodiments of any of the embodiments herein, the telomerase inhibitor is administered with a pharmaceutically acceptable excipient. In some embodiments of any of the embodiments herein, the telomerase inhibitor is formulated for oral, intravenous, subcutaneous, intramuscular, topical, intraperitoneal, intranasal, inhalation, or intraocular administration. In some embodiments of any of the embodiments herein, administration of the therapeutically effective amount of the telomerase inhibitor comprises contacting one or more neoplastic progenitor cells with the telomerase inhibitor. In some embodiments of any of the embodiments herein, the effective amount of a telomerase inhibitor is 7.5 mg/kg to 9.3 mg/kg. In some embodiments of any of the embodiments herein, the effective amount of a telomerase inhibitor is 9.5 mg/kg to 11.7 mg/kg. In some embodiments of any of the embodiments herein, administration of the telomerase inhibitor does not inhibit cytokine-dependent megakaryocyte growth. In some embodiments of any of the embodiments herein, the individual carries a V617F gain of function mutation in the Janus kinase 2 (JAK2) gene. In some embodiments, administration of the telomerase inhibitor decreases the percentage of JAK2 V617F allelic burden in the individual. In some embodiments of any of the embodiments herein, administration of the telomerase inhibitor inhibits cytokine-independent megakaryocyte growth. In some embodiments of any of the embodiments herein, administration of the telomerase inhibitor inhibits CFU-mega. In some embodiments, inhibition of CFU-Mega is independent of reduction in JAK2 allelic burden. In some embodiments, the individual is resistant or intolerant to a prior non-telomerase inhibitor-based therapy. In some embodiments, the prior non-telomerase inhibitor-based therapy is hydroxyurea, anagrelide, or Interferon α-2B. In some embodiments, the individual is a human.

Accordingly, in one aspect, provided herein are methods for alleviating at least one symptom associated with polycythemia vera (PV) in an individual in need thereof, the method comprising: administering a clinically effective amount of a telomerase inhibitor to the individual, wherein administration of the telomerase inhibitor alleviates at least one symptom associated with polycythemia vera. In some embodiments, the symptom comprises headache, dizziness or lightheadedness, chest pain, weakness, fainting, vision changes, numbness or tingling of extremities, shortness of breath, weakness or feeling tired, enlarged spleen, nosebleeds, bruising, bleeding from mouth or gums, or bloody stool. In some embodiments of any of the embodiments herein, the telomerase inhibitor comprises an oligonucleotide. In some embodiments, the oligonucleotide is complementary to the RNA component of telomerase. In some embodiments, the oligonucleotide is 10-20 base pairs in length. In some embodiments, the oligonucleotide comprises the sequence TAGGGTTAGACAA (SEQ ID NO:12). In some embodiments of any of the embodiments herein, the oligonucleotide comprises at least one N3'→P5' thiophosphoramidate internucleoside linkage. In some embodiments of any of the embodiments herein, oligonucleotide comprises N3'→P5' thiophosphoramidate internucleoside linkages. In some embodiments of any of the embodiments herein, the oligonucleotide further comprises a lipid moiety linked to the 5' and/or 3' end of the oligonucleotide. In some embodiments of any of the embodiments herein, the lipid moiety is linked to the 5' and/or 3' end of the oligonucleotide via a linker. In some embodiments, the linker is a glycerol or aminoglycerol linker. In some embodiments of any of the embodiments herein, the lipid moiety is a palmitoyl (C16) moiety. In some embodiments of any of the embodiments herein, the telomerase inhibitor is imetelstat. In some embodiments of any of the embodiments herein, the telomerase inhibitor is administered with a pharmaceutically acceptable excipient. In some embodiments of any of the embodiments herein, the telomerase inhibitor is formulated for oral, intravenous, subcutaneous, intramuscular, topical, intraperitoneal, intranasal, inhalation, or intraocular administration. In some embodiments of any of the embodiments herein, administration of the therapeutically effective amount of the telomerase inhibitor comprises contacting one or more neoplastic progenitor cells with the telomerase inhibitor. In some embodiments of any of the embodiments herein, the effective amount of a telomerase inhibitor is 7.5 mg/kg to 9.3 mg/kg. In some embodiments of any of the embodiments herein, the effective amount of a telomerase inhibitor is 9.5 mg/kg to 11.7 mg/kg. In some embodiments of any of the embodiments herein, administration of the telomerase inhibitor inhibits erythroid growth. In some embodiments of any of the embodiments herein, administration of the telomerase inhibitor inhibits CFU-erythroid. In some embodiments of any of the embodiments herein, the individual carries a V617F gain of function mutation in the Janus kinase 2 (JAK2) gene. In some embodiments, administration of the telomerase inhibitor decreases the percentage of JAK2 V617F allelic burden in the individual. In some embodiments, the individual is resistant or intolerant to a prior non-telomerase inhibitor-based therapy. In some embodiments, the individual is a human.

Accordingly, in one aspect, provided herein are methods for alleviating at least one symptom associated with myelofibrosis in an individual in need thereof, the method comprising: administering a clinically effective amount of a telomerase inhibitor to the individual, wherein administration of the telomerase inhibitor alleviates at least one symptom associated with myelofibrosis. In some embodiments, the symptom comprises enlarged spleen and splenic pain, early satiety, anemia, bone pain, fatigue, fever, night sweats, weight loss, weakness, fainting, nosebleeds, bruising, bleeding from mouth or gums, bloody stool, or stroke. In some embodiments of any of the embodiments herein, the telomerase inhibitor comprises an oligonucleotide. In some embodiments, the oligonucleotide is complementary to the RNA component of telomerase. In some embodiments, the oligonucleotide is 10-20 base pairs in length. In some embodiments, the oligonucleotide comprises the sequence TAGGGTTAGACAA (SEQ ID NO:12). In some embodiments of any of the embodiments herein, the oligonucleotide comprises at least one N3' P5' thiophosphoramidate internucleoside linkage. In some embodiments of any of the embodiments herein, oligonucleotide comprises N3'→P5' thiophosphoramidate internucleoside linkages. In some embodiments of any of the embodiments herein, the oligonucleotide further comprises a lipid moiety linked to the 5' and/or 3' end of the oligonucleotide. In some embodiments of any of the embodiments herein, the lipid moiety is linked to the 5' and/or 3' end of the oligonucleotide via a linker. In some embodiments, the linker is a glycerol or aminoglycerol linker. In some embodiments of any of the embodiments herein, the lipid moiety is a palmitoyl (C16) moiety. In some embodiments of any of the embodiments herein, the telomerase inhibitor is imetelstat. In some embodiments of any of the embodiments herein, the telomerase inhibitor is administered with a pharmaceutically acceptable excipient. In some embodiments of any of the embodiments herein, the telomerase inhibitor is formulated for oral, intravenous, subcutaneous, intramuscular, topical, intraperitoneal, intranasal, inhalation, or intraocular administration. In some embodiments of any of the embodiments herein, administration of the therapeutically effective amount of the telomerase inhibitor comprises contacting one or more neoplastic progenitor cells with the telomerase inhibitor. In some embodiments of any of the embodiments herein, the effective amount of a telomerase inhibitor is 7.5 mg/kg to 9.3 mg/kg. In some embodiments of any of the embodiments herein, the effective amount of a telomerase inhibitor is 9.5 mg/kg to 11.7 mg/kg. In some embodiments of any of the embodiments herein, administration of the telomerase inhibitor does not inhibit cytokine-dependent megakaryocyte growth. In some embodiments of any of the embodiments herein, the individual carries a V617F gain of function mutation in the Janus kinase 2 (JAK2) gene. In some embodiments, administration of the telomerase inhibitor decreases the percentage of JAK2 V617F allelic burden in the individual. In some embodiments of any of the embodiments herein, administration of the telomerase inhibitor inhibits cytokine-independent megakaryocyte growth. In some embodiments of any of the embodiments herein, administration of the telomerase inhibitor inhibits CFU-mega. In some embodiments, inhibition of CFU-Mega is independent of reduction in JAK2 allelic burden. In some embodiments, the individual is resistant or intolerant to a prior non-telomerase inhibitor-based therapy. In some embodiments, the individual is a human.

In another aspect provided herein are methods for reducing bone marrow fibrosis in an individual diagnosed with or suspected of having a myeloproliferative neoplasm or myelodysplastic syndrome, the method comprising administering a clinically effective amount of a telomerase inhibitor to the individual, wherein administration of the telomerase inhibitor reduces bone marrow fibrosis in the individual. In another aspect, provided herein are methods in patients with MF for maintaining platelet counts of greater than about $100 \times 10^9$/L in the blood of the individual the method comprising administering a clinically effective amount of a telomerase inhibitor to the individual, wherein administration of the telomerase inhibitor increases platelet counts. In another aspect, provided herein are methods in patients with MF for maintaining hemoglobin level of at least 90 g/L, or 100 g/L or 110 g/L or 120 g/L the method comprising administering a clinically effective amount of a telomerase inhibitor to the individual, wherein administration of the telomerase inhibitor increases hemoglobin levels. In another aspect, provided herein are methods in patients with MF for maintaining absolute neutrophil count of at least $1.0 \times 10^9$/L or at least $2.0 \times 10^9$/L the method comprising administering a clinically effective amount of a telomerase inhibitor to the individual, wherein administration of the telomerase inhibitor increases neutrophil counts. In some aspects, the telomerase inhibitor is administered no more than once every two weeks. In other aspects, the telomerase inhibitor is administered to maintain blood platelet counts of between about $150 \times 10^3$/µL to about $400 \times 10^3$/µL in the blood of an individual. In some embodiments of any of the embodiments herein, the telomerase inhibitor comprises an oligonucleotide. In some embodiments, the oligonucleotide is complementary to the RNA component of telomerase. In some embodiments, the oligonucleotide is 10-20 base pairs in length. In some embodiments, the oligonucleotide comprises the sequence TAGGGTTAGACAA (SEQ ID NO:12). In some embodiments of any of the embodiments herein, the oligonucleotide comprises at least one N3'→P5' thiophosphoramidate internucleoside linkage. In some embodiments of any of the embodiments herein, oligonucleotide comprises N3'→P5' thiophosphoramidate internucleoside linkages. In some embodiments of any of the embodiments herein, the oligonucleotide further comprises a lipid moiety linked to the 5' and/or 3' end of the oligonucleotide. In some embodiments of any of the embodiments herein, the lipid moiety is linked to the 5' and/or 3' end of the oligonucleotide via a linker. In some embodiments, the linker is a glycerol or aminoglycerol linker. In some embodiments of any of the embodiments herein, the lipid moiety is a palmitoyl (C16) moiety. In some embodiments of any of the embodiments herein, the telomerase inhibitor is imetelstat. In some embodiments of any of the embodiments herein, the telomerase inhibitor is administered with a pharmaceutically acceptable excipient. In some embodiments of any of the embodiments herein, the telomerase inhibitor is formulated for oral, intravenous, subcutaneous, intramuscular, topical, intraperitoneal, intranasal, inhalation, or intraocular administration. In some embodiments of any of the embodiments herein, administration of the therapeutically effective amount of the telomerase inhibitor comprises contacting one or more neoplastic progenitor cells with the telomerase inhibitor. In some embodiments of any of the embodiments herein, the effective amount of a telomerase inhibitor is 7.5 mg/kg to 9.3 mg/kg. In some embodiments of any of the embodiments herein, the effective amount of a telomerase inhibitor is 9.5 mg/kg to 11.7 mg/kg.

Accordingly, in one aspect, provided herein are methods for alleviating at least one symptom associated with acute myeloid leukemia in an individual in need thereof, the method comprising: administering a clinically effective amount of a telomerase inhibitor to the individual, wherein administration of the telomerase inhibitor alleviates at least one symptom associated with acute myeloid leukemia. In some embodiments, the symptoms comprise enlarged spleen and splenic pain, anemia, bone pain, fatigue, fever, night sweats, weight loss, weakness, fainting, nosebleeds, bruising, bleeding from mouth or gums, bloody stool, or stroke. In some embodiments of any of the embodiments herein, the telomerase inhibitor comprises an oligonucleotide. In some embodiments, the oligonucleotide is complementary to the RNA component of telomerase. In some embodiments, the oligonucleotide is 10-20 base pairs in length. In some embodiments, the oligonucleotide comprises the sequence TAGGGTTAGACAA (SEQ ID NO:12). In some embodiments of any of the embodiments herein, the oligonucleotide comprises at least one N3' P5' thiophosphoramidate internucleoside linkage. In some embodiments of any of the embodiments herein, oligonucleotide comprises N3'→P5' thiophosphoramidate internucleoside linkages. In some embodiments of any of the embodiments herein, the oligonucleotide further comprises a lipid moiety linked to the 5' and/or 3' end of the oligonucleotide. In some embodiments of any of the embodiments herein, the lipid moiety is linked to the 5' and/or 3' end of the oligonucleotide via a linker. In some embodiments, the linker is a glycerol or aminoglycerol linker. In some embodiments of any of the embodiments herein, the lipid moiety is a palmitoyl (C16) moiety. In some embodiments of any of the embodiments herein, the telomerase inhibitor is imetelstat. In some embodiments of any of the embodiments herein, the telomerase inhibitor is administered with a pharmaceutically acceptable excipient. In some embodiments of any of the embodiments herein, the telomerase inhibitor is formulated for oral, intravenous, subcutaneous, intramuscular, topical, intraperitoneal, intranasal, inhalation, or intraocular administration. In some embodiments of any of the embodiments herein, administration of the therapeutically effective amount of the telomerase inhibitor comprises contacting one or more neoplastic progenitor cells with the telomerase inhibitor. In some embodiments of any of the embodiments herein, the effective amount of a telomerase inhibitor is 7.5 mg/kg to 9.3 mg/kg. In some embodiments of any of the embodiments herein, the effective amount of a telomerase inhibitor is 9.5 mg/kg to 11.7 mg/kg. In some embodiments herein, administration of the telomerase inhibitor does not inhibit cytokine-dependent megakaryocyte growth. In some embodiments herein, the individual carries a V617F gain of function mutation in the Janus kinase 2 (JAK2) gene. In some embodiments, administration of the telomerase inhibitor decreases the percentage of JAK2 V617F allelic burden in the individual. In some embodiments of any of the embodiments herein, administration of the telomerase inhibitor inhibits cytokine-independent megakaryocyte growth. In some embodiments of any of the embodiments herein, administration of the telomerase inhibitor inhibits CFU-mega. In some embodiments, inhibition of CFU-Mega is independent of reduction in JAK2 allelic burden. In some embodiments, the individual is resistant or intolerant to a prior non-telomerase inhibitor-based therapy. In some embodiments, the individual is a human.

Accordingly, in one aspect, provided herein are methods for alleviating at least one symptom associated with myelodysplastic syndrome, such as, for example, refractory anemia, refractory anemia with excess blasts, refractory cytopenia with multilineage dysplasia, refractory cytopenia with unilineage dysplasia, and chronic myelomonocytic leukemia. in an individual in need thereof, the method comprising: administering a clinically effective amount of a telomerase inhibitor to the individual, wherein administration of the telomerase inhibitor alleviates at least one symptom associated with myelodysplastic syndrome. In some embodiments, the symptoms comprise shortness of breath, fatigue, weakness, fainting, nosebleeds, bruising, bleeding from mouth or gums, bloody stool, petechiae, or stroke. In some embodiments of any of the embodiments herein, the telomerase inhibitor comprises an oligonucleotide. In some embodiments, the oligonucleotide is complementary to the RNA component of telomerase. In some embodiments, the oligonucleotide is 10-20 base pairs in length. In some embodiments, the oligonucleotide comprises the sequence TAGGGTTAGACAA (SEQ ID NO:12). In some embodiments of any of the embodiments herein, the oligonucleotide comprises at least one N3'→P5' thiophosphoramidate internucleoside linkage. In some embodiments of any of the embodiments herein, oligonucleotide comprises N3'→P5' thiophosphoramidate internucleoside linkages. In some embodiments of any of the embodiments herein, the oligonucleotide further comprises a lipid moiety linked to the 5' and/or 3' end of the oligonucleotide. In some embodiments of any of the embodiments herein, the lipid moiety is linked to the 5' and/or 3' end of the oligonucleotide via a linker. In some embodiments, the linker is a glycerol or aminoglycerol linker. In some embodiments of any of the embodiments herein, the lipid moiety is a palmitoyl (C16) moiety. In some embodiments of any of the embodiments herein, the telomerase inhibitor is imetelstat. In some embodiments of any of the embodiments herein, the telomerase inhibitor is administered with a pharmaceutically acceptable excipient. In some embodiments of any of the embodiments herein, the telomerase inhibitor is formulated for oral, intravenous, subcutaneous, intramuscular, topical, intraperitoneal, intranasal, inhalation, or intraocular administration. In some embodiments of any of the embodiments herein, administration of the therapeutically effective amount of the telomerase inhibitor comprises contacting one or more neoplastic progenitor cells with the telomerase inhibitor. In some embodiments of any of the embodiments herein, the effective amount of a telomerase inhibitor is 7.5 mg/kg to 9.3 mg/kg. In some embodiments of any of the embodiments herein, the effective amount of a telomerase inhibitor is 9.5 mg/kg to 11.7 mg/kg. In some embodiments of any of the embodiments herein, administration of the telomerase inhibitor inhibits cytokine-independent megakaryocyte growth. In some embodiments, the individual is resistant or intolerant to a prior non-telomerase inhibitor-based therapy. In some embodiments, the individual is a human.

DESCRIPTION OF THE DRAWINGS

FIG. 4A depicts the JAK2 V617F % allelic burden as a function of time in months from the baseline timepoint. FIG. 4B describes the median allelic burden (%) as a function of time from the baseline timepoint.

DETAILED DESCRIPTION OF THE INVENTION

Figure 1:
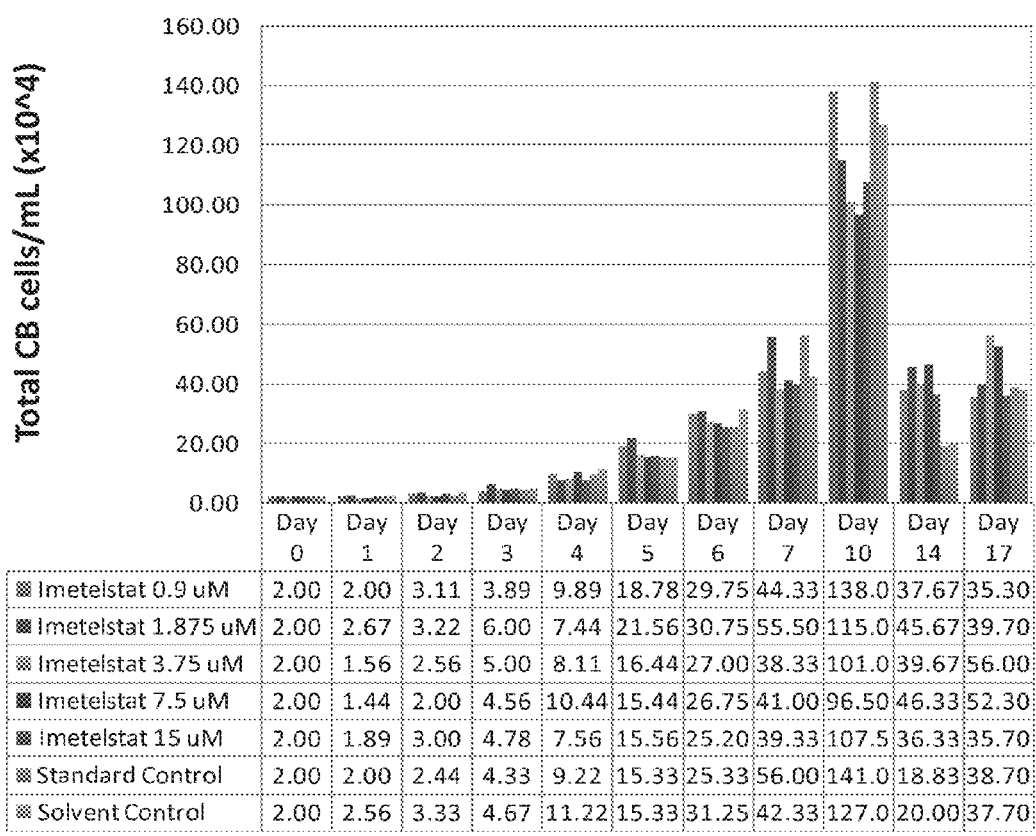
FIGS. 1A and 1B depict imetelstat effect on megakaryocyte growth and differentiation.
Figure 1:
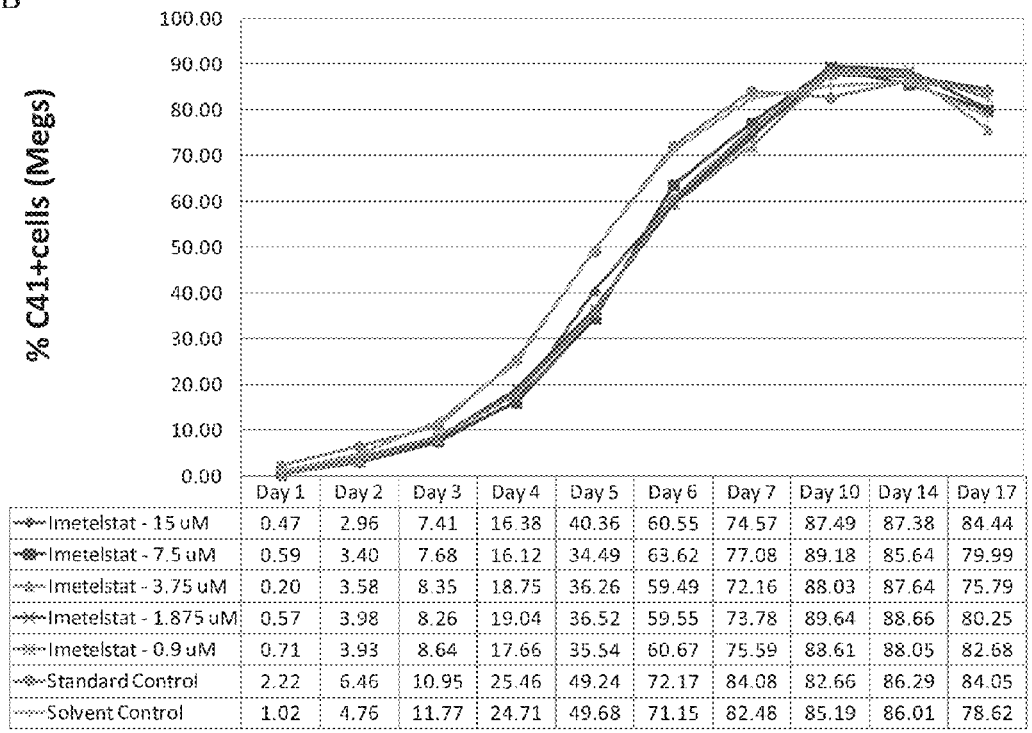

This invention provides, inter alia, methods for reducing neoplastic progenitor cell proliferation and alleviating symptoms in individuals. The invention provided herein discloses, inter alia, methods for using telomerase inhibitor compounds to treat and alleviate symptoms associated with myeloproliferative neoplasms (MPN) such as Essential Thrombocythemia (ET), Polycythemia Vera, Myelofibrosis, and Acute Myelogenous leukemia by targeting the neoplastic progenitor cells characteristic of these diseases. The invention provided herein also discloses, inter alia, methods for using telomerase inhibitor compounds to treat and alleviate symptoms associated with myelodysplastic syndromes (MDS) such as, for example, refractory anemia, refractory anemia with excess blasts, refractory cytopenia with multilineage dysplasia, refractory cytopenia with unilineage dysplasia, and chronic myelomonocytic leukemia by targeting the neoplastic progenitor cells responsible for producing the abnormally high numbers of cells characteristic of these diseases. The inventors have made the surprising discovery that telomerase inhibitors (such as imetelstat) can effectively reduce circulating blood platelet levels in individuals with MPN and MDS. Additionally, this reduction in platelet levels is seen independently of the common ET-associated mutation in the Janus kinase 2 gene (JAK2; seen in approximately 50% of ET cases) and is effective in individuals who were previously resistant to treatment with hydroxyurea, which is a common front-line therapy for ET. Also provided herein are methods for using telomerase inhibitors (for example, imetelstat) for maintaining blood platelet counts at relatively normal ranges in the blood of individuals diagnosed with or suspected of having ET. Without being bound to theory and unlike other common treatments for MPN and MDS, the telomerase inhibitor compounds used in the methods of the present invention appear to specifically inhibit the neoplastic progenitor cells driving the malignancy responsible for this condition.

I. GENERAL TECHNIQUES

The practice of the invention will employ, unless otherwise indicated, conventional techniques in nucleic acid chemistry, molecular biology, microbiology, cell biology, biochemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994). Nucleic acids can be synthesized in vitro by well-known chemical synthesis techniques, as described in, e.g., Carruthers (1982) Cold Spring Harbor *Symp. Quant. Biol.* 47:411-418; Adams (1983) *J. Am. Chem. Soc.* 105:661; Belousov (1997) *Nucleic Acids Res.* 5 25:3440-3444; Frenkel (1995) *Free Radic. Biol. Med.* 19:373-380; Blommers (1994) *Biochemistry* 33:7886-7896; Narang (1979) *Meth. Enzymol.* 68:90; Brown (1979) *Meth. Enzymol.* 68:109; Beaucage (1981) *Tetra. Lett.* 22:1859; Komberg and Baker, *DNA Replication*, 2nd Ed. (Freeman, San Francisco, 1992); Scheit, *Nucleotide Analogs* (John Wiley, New York, 1980); Uhlmann and Peyman, *Chemical Reviews*, 90:543-584, 1990.

II. DEFINITIONS

The term "nucleoside" refers to a moiety having the general structure represented below, where B represents a nucleobase and the 2' carbon can be substituted as described below. When incorporated into an oligomer or polymer, the 3' carbon is further linked to an oxygen or nitrogen atom.

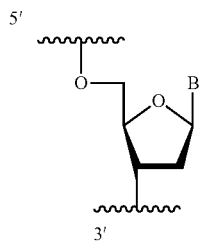

This structure includes 2'-deoxy and 2'-hydroxyl (i.e. deoxyribose and ribose) forms, and analogs. Less commonly, a 5'—NH group can be substituted for the 5'-oxygen. "Analogs", in reference to nucleosides, includes synthetic nucleosides having modified nucleobase moieties (see definition of "nucleobase" below) and/or modified sugar moieties, such as 2'-fluoro sugars, and further analogs. Such analogs are typically designed to affect binding properties, e.g., stability, specificity, or the like. The term nucleoside includes the natural nucleosides, including 2'-deoxy and 2'-hydroxyl forms, e.g., as described in Komberg and Baker, *DNA Replication*, 2nd Ed. (Freeman, San Francisco, 1992), and analogs. "Analogs", in reference to nucleosides, includes synthetic nucleosides having modified nucleobase moieties (see definition of "nucleobase," infra) and/or modified sugar moieties, e.g., described generally by Scheit, *Nucleotide Analogs* (John Wiley, New York, 1980). Such analogs include synthetic nucleosides designed to enhance binding properties, e.g., stability, specificity, or the like, such as disclosed by Uhlmann and Peyman, Chemical Reviews 90:543-584, 1990). An oligonucleotide containing such nucleosides, and which typically contains synthetic nuclease-resistant internucleoside linkages, may itself be referred to as an "analog".

A "polynucleotide" or "oligonucleotide" refers to a ribose and/or deoxyribose nucleoside subunit polymer or oligomer having between about 2 and about 200 contiguous subunits. The nucleoside subunits can be joined by a variety of intersubunit linkages, including, but not limited to, phosphodiester, phosphotriester, methylphosphonate, P3→N5' phosphoramidate, N3→P5' phosphoramidate, N3→P5' thiophosphoramidate, and phosphorothioate linkages. The term also includes such polymers or oligomers having modifications, known to one skilled in the art, to the sugar (e.g., 2' substitutions), the base (see the definition of "nucleoside," supra), and the 3' and 5' termini. In embodiments where the oligonucleotide moiety includes a plurality of intersubunit linkages, each linkage may be formed using the same chemistry, or a mixture of linkage chemistries may be used. When an oligonucleotide is represented by a sequence of letters, such as "ATGUCCTG," it will be understood that the nucleotides are in 5→3' order from left to right. Representation of the base sequence of the oligonucleotide in this manner does not imply the use of any particular type of internucleoside subunit in the oligonucleotide.

A "nucleobase" includes (i) native DNA and RNA nucleobases (uracil, thymine, adenine, guanine, and cytosine), (ii) modified nucleobases or nucleobase analogs (e.g., 5-methylcytosine, 5-bromouracil, or inosine) and (iii) nucleobase analogs. A nucleobase analog is a compound whose molecular structure mimics that of a typical DNA or RNA base.

The term "lipid" is used broadly herein to encompass substances that are soluble in organic solvents, but sparingly soluble, if at all, in water. The term lipid includes, but is not limited to, hydrocarbons, oils, fats (such as fatty acids and glycerides), sterols, steroids and derivative forms of these compounds. In some embodiments, lipids are fatty acids and their derivatives, hydrocarbons and their derivatives, and sterols, such as cholesterol. Fatty acids usually contain even numbers of carbon atoms in a straight chain (commonly 12-24 carbons) and may be saturated or unsaturated, and can contain, or be modified to contain, a variety of substituent groups. For simplicity, the term "fatty acid" also encompasses fatty acid derivatives, such as fatty or esters. In some embodiments, the term "lipid" also includes amphipathic compounds containing both lipid and hydrophilic moieties.

A "telomerase inhibitor" is a compound which is capable of reducing or inhibiting the activity of telomerase reverse transcriptase enzyme in a mammalian cell. Such an inhibitor may be a small molecule compound, such as described herein, or an hTR template inhibitor including an oligonucleotide, such as described herein. In one aspect, the telomerase inhibitor is Imetelstat.

An "hTR template inhibitor" is a compound that blocks the template region of the RNA component of human telomerase, thereby inhibiting the activity of the enzyme. The inhibitor is typically an oligonucleotide that is able to hybridize to this region. In some embodiments, the oligonucleotide includes a sequence effective to hybridize to a more specific portion of this region, having sequence 5'-CUAACCCUAAC-3' (SEQ ID NO:21).

A compound is said to "inhibit the proliferation of cells" if the proliferation of cells in the presence of the compound is less than that observed in the absence of the compound. That is, proliferation of the cells is either slowed or halted in the presence of the compound. Inhibition of cancer-cell proliferation may be evidenced, for example, by reduction in the number of cells or rate of expansion of cells, reduction in tumor mass or the rate of tumor growth, or increase in survival rate of a subject being treated.

An oligonucleotide having "nuclease-resistant linkages" refers to one whose backbone has subunit linkages that are substantially resistant to nuclease cleavage, in non-hybridized or hybridized form, by common extracellular and intracellular nucleases in the body; that is, the oligonucleotide shows little or no nuclease cleavage under normal nuclease conditions in the body to which the oligonucleotide is exposed. The N3'→P5' phosphoramidate (NP) or N3'→P5' thiophosphoramidate (NPS) linkages described below are nuclease resistant.

An "individual" can be a mammal, such as any common laboratory model organism. Mammals include, but are not limited to, humans and non-human primates, farm animals, sport animals, pets, mice, rats, and other rodents. In some embodiments, an individual is a human.

An "effective amount" or "therapeutically effective amount" or "clinically effective amount" refers to an amount of therapeutic compound, such as telomerase inhibitor, administered to a mammalian subject, either as a single dose or as part of a series of doses, which is effective to produce a desired therapeutic effect.

As used herein, "neoplastic cells" refer to cells which exhibit relatively autonomous growth, so that they exhibit an aberrant growth phenotype characterized by a significant loss of control of cell proliferation. Neoplastic cells comprise cells which may be actively replicating or in a temporary non-replicative resting state ($G_1$ or $G_0$); similarly, neoplastic cells may comprise cells which have a well-differentiated phenotype, a poorly-differentiated phenotype, or a mixture of both type of cells. Thus, not all neoplastic cells are necessarily replicating cells at a given timepoint. "Neoplastic cells" encompass such cells in benign neoplasms and cells in malignant neoplasms.

As used herein, "neoplastic progenitor cells" refers to cells of a cellular composition that possess the ability to become neoplastic.

As used herein, the term "neoplasm" or "neoplasia" or "neoplastic" refers to abnormal new cell growth. Unlike hyperplasia, neoplastic proliferation persists even in the absence of an original stimulus.

As used herein, the singular form "a", "an", and "the" includes plural references unless indicated otherwise.

It is understood that aspects and embodiments of the invention described herein include "comprising," "consisting," and "consisting essentially of" aspects and embodiments.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. TELOMERASE INHIBITOR COMPOUNDS

Telomerase is a ribonucleoprotein that catalyzes the addition of telomeric repeat sequences (having the sequence 5'-TTAGGG-3' in humans) to chromosome ends. See e.g. Blackburn, 1992, *Ann. Rev. Biochem.* 61:113-129. The enzyme is expressed in most cancer cells but not in mature somatic cells. Loss of telomeric DNA may play a role in triggering cellular senescence; see Harley, 1991, *Mutation Research* 256:271-282. A variety of cancer cells have been shown to be telomerase-positive, including cells from cancer of the skin, connective tissue, adipose, breast, lung, stomach, pancreas, ovary, cervix, uterus, kidney, bladder, colon, prostate, central nervous system (CNS), retina and hematologic tumors (such as myeloma, leukemia and lymphoma). Targeting of telomerase can be effective in providing treatments that discriminate between malignant and normal cells to a high degree, avoiding many of the deleterious side effects that can accompany chemotherapeutic regimens which target dividing cells indiscriminately.

Inhibitors of telomerase identified to date include oligonucleotides (for example, oligonucleotides having nuclease resistant linkages) as well as small molecule compounds. Further information regarding telomerase inhibitor compounds can be found in U.S. Pat. No. 7,998,938, the disclosure of which is incorporated by reference herein in its entirety.

A. Small Molecule Compounds

Small molecule inhibitors of telomerase include, for example, BRACO19 ((9-(4-(N,N-dimethylamino)phenylamino)-3,6-bis(3-pyrrolodino propionamido)acridine (see *Mol. Pharmacol.* 61(5):1154-62, 2002); DODC (diethyloxadicarbocyanine), and telomestatin. These compounds may act as G-quad stabilizers, which promote the formation of an inactive G-quad configuration in the RNA component of telomerase. Other small molecule inhibitors of telomerase include BIBR1532 (2-[(E)-3-naphthen-2-yl but-2-enoylamino]benzoic acid) (see Ward & Autexier, *Mol. Pharmacol.* 68:779-786, 2005; also *J. Biol. Chem.* 277(18):15566-72, 2002); AZT and other nucleoside analogs, such as ddG and ara-G (see, for example, U.S. Pat. Nos. 5,695,932 and 6,368, 789), and certain thiopyridine, benzo[b]thiophene, and pyrido[b]thiophene derivatives, described by Gaeta et al. in U.S. Pat. Nos. 5,767,278, 5,770,613, 5,863,936, 5,656,638 and 5,760,062, the disclosures of which are incorporated by reference herein. Another example is 3-chlorobenzo[b] thiophene-2-carboxy-2'-[(2,5-dichlorophenyl amino)thia] hydrazine, described in U.S. Pat. No. 5,760,062 and which is incorporated by reference herein.

B. Oligonucleotide-Based Telomerase Inhibitors: Sequence and Composition

The genes encoding both the protein and RNA components of human telomerase have been cloned and sequenced (see U.S. Pat. Nos. 6,261,836 and 5,583,016, respectively, both of which are incorporated herein by reference). Oligonucleotides can be targeted against the mRNA encoding the telomerase protein component (the human form of which is known as human telomerase reverse transcriptase, or hTERT) or the RNA component of the telomerase holoenzyme (the human form of which is known as human telomerase RNA, or hTR).

The nucleotide sequence of the RNA component of human telomerase (hTR) is shown in the Sequence Listing below (SEQ ID NO: 1), in the 5'→3' direction. The sequence is shown using the standard abbreviations for ribonucleotides; those of skill in the art will recognize that the sequence also represents the sequence of the cDNA, in which the ribonucleotides are replaced by deoxyribonucleotides, with uridine (U) being replaced by thymidine (T). The template sequence of the RNA component is located within the region defined by nucleotides 46-56 (5'-CUAACCCUAAC-3') (SEQ ID NO:21), which is complementary to a telomeric sequence composed of about one-and-two-thirds telomeric repeat units. The template region functions to specify the sequence of the telomeric repeats that telomerase adds to the chromosome ends and is essential to the activity of the telomerase enzyme (see e.g. Chen et al., *Cell* 100: 503-514, 2000; Kim et al., *Proc. Natl. Acad. Sci. USA* 98 (14):7982-7987, 2001). The design of antisense, ribozyme or small interfering RNA (siRNA) agents to inhibit or cause the destruction of mRNAs is well known (see, for example, Lebedeva, I, et al. *Annual Review of Pharmacology and Toxicology*, Vol. 41: 403-419, April 2001; Macejak, D, et al., *Journal of Virology*, Vol. 73 (9): 7745-7751, September 1999, and Zeng, Y. et al., PNAS Vol. 100 (17) p. 9779-9784, Aug. 19, 2003) and such agents may be designed to target the hTERT mRNA and thereby inhibit production of hTERT protein in a target cell, such as a cancer cell (see, for example, U.S. Pat. Nos. 6,444,650 and 6,331,399).

Oligonucleotides targeting hTR (that is, the RNA component of the enzyme) act as inhibitors of telomerase enzyme activity by blocking or otherwise interfering with the interaction of hTR with the hTERT protein, which interaction is necessary for telomerase function (see, for example, Villeponteau et al., U.S. Pat. No. 6,548,298).

A preferred target region of hTR is the template region, spanning nucleotides 30-67 of SEQ ID NO:1 (GGGUUGCG-GAGGGUGGGCCUGGGAGGGGUGGUGGCCAUUU UUUGUCUAAC-CCUAACUGAGAAGGGCGUAGGCGC-CGUGCUUUUGCUCCCC GCGCGCUGUUUUU-CUCGCUGACUUUCAGCGGGCGGAAAAGCCUCGG-CCUG CCGCCUUCCACCGUUCAUUCUAGAG-CAAACAAAAAAUGUCAGCUGCUGGC CCGUUCGC-CUCCCGGGGACCUGCGGCGGGUCGC-CUGCCCAGCCCCCGAAC CCCGCCUGGAGCCGCGGUCGGC-CCGGGGCUUCUCCGGAGGCACCCACUGC CACCGC-GAAGAGUUGGGCUCUGUCAGCCGCGGGU-CUCUCGGGGGCGAGGG CGAGGUUCACCGUUUCAGGCCGCAGGAA-GAGGAACGGAGCGAGUCCCGCC GCGGCGCGA-UUCCCUGAGCUGUGGGACGUGCACCCAG-GACUCGGCUCACA CAUGCAGUUCGCUUUCCUGUUG-GUGGGGGGAACGCCGAUCGUGCGCAUCC GUCAC-CCCUCGCCGGCAGUGGGGGCUUGUGAAC-CCCCAAACCUGACUGAC UGGGCCAGUGUGCU). Oligonucleotides targeting this region are referred to herein as "hTR template inhibitors" (see e.g. Herbert et al., *Oncogene* 21 (4):638-42 (2002)). Preferably, such an oligonucleotide includes a sequence which is complementary or near-complementary to some portion of the 11-nucleotide region having the sequence 5'-CUAACCCUAAC-3' SEQ ID NO:21).

Another preferred target region is the region spanning nucleotides 137-179 of hTR (see Pruzan et al., *Nucl. Acids Research*, 30:559-568, 2002). Within this region, the sequence spanning 141-153 is a preferred target. PCT publication WO 98/28442 describes the use of oligonucleotides of at least 7 nucleotides in length to inhibit telomerase, where the oligonucleotides are designed to be complementary to accessible portions of the hTR sequence outside of the template region, including nucleotides 137-196, 290-319, and 350-380 of hTR. Preferred hTR targeting sequence are given below, and identified by SEQ ID NOS: 2-22.

The region of the therapeutic oligonucleotide that is targeted to the hTR sequence is preferably exactly complementary to the corresponding hTR sequence. While mismatches may be tolerated in certain instances, they are expected to decrease the specificity and activity of the resultant oligonucleotide conjugate. In particular embodiments, the base sequence of the oligonucleotide is thus selected to include a sequence of at least 5 nucleotides exactly complementary to the hTR target, and enhanced telomerase inhibition may be obtained if increasing lengths of complementary sequence are employed, such as at least 8, at least 10, at least 12, at least 13 or at least 15 nucleotides exactly complementary to the hTR target. In other embodiments, the sequence of the oligonucleotide includes a sequence of from at least 5 to 20, from at least 8 to 20, from at least 10 to 20 or from at least 10 to 15 nucleotides exactly complementary to the hTR target sequence.

Optimal telomerase inhibitory activity may be obtained when the full length of the oligonucleotide is selected to be complementary to the hTR target sequence. However, it is not necessary that the full length of the oligonucleotide is exactly complementary to the target sequence, and the oligonucleotide sequence may include regions that are not complementary to the target sequence. Such regions may be added, for example, to confer other properties on the compound, such as sequences that facilitate purification. Alternatively, an oligonucleotide may include multiple repeats of a sequence complementary to an hTR target sequence.

If the oligonucleotide is to include regions that are not complementary to the target sequence, such regions are typically positioned at one or both of the 5' or 3' termini. Exemplary sequences targeting human telomerase RNA (hTR) include the following:

| hTR Targeting Sequence | Region of SEQ ID NO: 1 | SEQ ID NO: |
|---|---|---|
| ACATTTTTTGTTTGCTCTAG | 160-179 | 2 |
| GCTCTAGAATGAACGGTGGAAGGCGGCAGG | 137-166 | 3 |
| GTGGAGGCGGCAGG | 137-151 | 4 |
| GGAAGGCGGCAGG | 137-149 | 5 |
| GTGGAAGGCGGCA | 139-151 | 6 |
| GTGGAAGGCGG | 141-151 | 7 |
| CGGTGGAAGGCGG | 141-153 | 8 |
| ACGGTGGAAGGCG | 142-154 | 9 |
| AACGGTGGAAGGCGG | 143-155 | 10 |
| ATGAACGGTGGAAGGCGG | 144-158 | 11 |
| TAGGGTTAGACAA | 42-54 | 12 |
| CAGTTAGGGTTAG | 46-58 | 13 |
| TAGGGTTAGACA | 42-53 | 14 |
| TAGGGTTAGAC | 42-52 | 15 |
| GTTAGGGTTAG | 46-56 | 16 |
| GTTAGGGTTAGAC | 44-56 | 17 |
| GTTAGGGTTAGACAA | 42-56 | 18 |
| GGGTTAGAC | 44-52 | n/a |
| CAGTTAGGG | 50-58 | n/a |

| hTR Targeting Sequence | Region of SEQ ID NO: 1 | SEQ ID NO: |
|---|---|---|
| CCCTTCTCAGTT | 54-65 | 19 |
| CGCCCTTCTCAG | 56-67 | 20 |

The internucleoside linkages in the oligonucleotide may include any of the available oligonucleotide chemistries, e.g. phosphodiester, phosphotriester, methylphosphonate, P3→N5' phosphoramidate, N3→P5' phosphoramidate, N3→P5' thiophosphoramidate, and phosphorothioate. Typically, but not necessarily, all of the internucleoside linkages within the oligonucleotide will be of the same type, although the oligonucleotide component may be synthesized using a mixture of different linkages.

In some embodiments, the oligonucleotide has at least one N3→P5' phosphoramidate (NP) or N3→P5' thiophosphoramidate (NPS) linkage, which linkage may be represented by the structure: 3'-(—NH—P(=O)(—XR)—O—)-5', wherein X is O or S and R is selected from the group consisting of hydrogen, alkyl, and aryl; and pharmaceutically acceptable salts thereof, when XR is OH or SH. In other embodiments, the oligonucleotide includes all NP or, in some embodiments, all NPS linkages.

In one embodiment, the sequence for an hTR template inhibitor oligonucleotide is the sequence complementary to nucleotides 42-54 of SEQ ID NO: 1 supra. The oligonucleotide having this sequence (TAGGGTTAGACAA; SEQ ID NO:12) and N3→P5' thiophosphoramidate (NPS) linkages is designated herein as GRN163. See, for example, Asai et al., *Cancer Research* 63:3931-3939 (2003) and Gryaznov et al., *Nucleosides Nucleotides Nucleic Acids* 22(5-8):577-81 (2003).

The oligonucleotide GRN163 administered alone has shown inhibitory activity in vitro in cell culture, including epidermoid carcinoma, breast epithelium, renal carcinoma, renal adenocarcinoma, pancreatic, brain, colon, prostate, leukemia, lymphoma, myeloma, epidermal, cervical, ovarian and liver cancer cells.

The oligonucleotide GRN163 has also been tested and shown to be therapeutically effective in a variety of animal tumor models, including ovarian and lung, both small cell and non-small cell (see, e.g., U.S. Pat. No. 7,998,938, the disclosure of which is incorporated by reference).

C. Lipid-Oligonucleotide Conjugates

In some aspects, the oligonucleotide-based telomerase inhibitors disclosed herein includes at least one covalently linked lipid group (see U.S. Pub. No. 2005/0113325, which is incorporated herein by reference). This modification provides superior cellular uptake properties, such that an equivalent biological effect may be obtained using smaller amounts of the conjugated oligonucleotide compared to the unmodified form. When applied to the human therapeutic setting, this may translate to reduced toxicity risks, and cost savings.

The lipid group L is typically an aliphatic hydrocarbon or fatty acid, including derivatives of hydrocarbons and fatty acids, with examples being saturated straight chain compounds having 14-20 carbons, such as myristic (tetradecanoic) acid, palmitic (hexadecanoic) acid, and stearic (octadeacanoic) acid, and their corresponding aliphatic hydrocarbon forms, tetradecane, hexadecane and octadecane. Examples of other suitable lipid groups that may be employed are sterols, such as cholesterol, and substituted fatty acids and hydrocarbons, particularly polyfluorinated forms of these groups. The scope of the lipid group L includes derivatives such as amine, amide, ester and carbamate derivatives. The type of derivative is often determined by the mode of linkage to the oligonucleotide, as exemplified below:

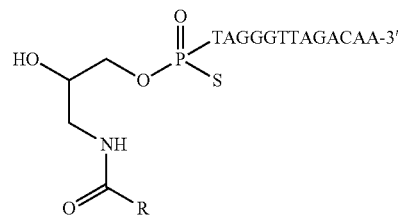

when —R is —(CH$_2$)$_{14}$CH$_3$ (palmitoyl) (SEQ ID NO:22). This compound is designated herein as GRN163L (imetelstat).

In one exemplary structure, the lipid moiety is palmitoyl amide (derived from palmitic acid), conjugated through an aminoglycerol linker to the 5' thiophosphate group of an NPS-linked oligonucleotide. The NPS oligonucleotide having the sequence shown for GRN163 and conjugated in this manner (as shown above) is designated GRN163L (Imetelstat) herein. In a second exemplary structure, the lipid, as a palmitoyl amide, is conjugated through the terminal 3' amino group of an NPS oligonucleotide.

D. Pharmaceutical Compositions

In some aspects of the present invention, when employed as pharmaceuticals, the telomerase inhibitor compounds disclosed herein can be formulated with a pharmaceutically acceptable excipient or carrier to be formulated into a pharmaceutical composition.

When employed as pharmaceuticals, the telomerase inhibitor compounds can be administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound. When employed as oral compositions, the telomerase inhibitor compounds disclosed herein are protected from acid digestion in the stomach by a pharmaceutically acceptable protectant.

This invention also includes pharmaceutical compositions which contain, as the active ingredient, a telomerase inhibitor compound associated with one or more pharmaceutically acceptable excipients or carriers. In making the compositions of this invention, the active ingredient is usually mixed with an excipient or carrier, diluted by an excipient or carrier or enclosed within such an excipient or carrier which can be in the form of a capsule, sachet, paper or other container. When the excipient or carrier serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active lyophilized compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 mg to about 100 mg or more, such as any of about 1 mg to about 5 mg, 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, or about 1 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

The telomerase inhibitor compounds are effective over a wide dosage range and are generally administered in a therapeutically effective amount. It will be understood, however, that the amount of the telomerase inhibitor compounds actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient telomerase inhibitor compound is mixed with a pharmaceutical excipient or carrier to form a solid preformulation composition containing a homogeneous mixture of a compound of the present invention. When referring to these preformulation compositions as homogeneous, it is meant that the active ingredient is dispersed evenly throughout the composition so that the composition can be readily subdivided into equally effective unit dosage forms such as tablets, pills and capsules.

The tablets or pills of the present invention can be coated or otherwise compounded to provide a dosage form affording the advantage of prolonged action and to protect the telomerase inhibitor compounds from acid hydrolysis in the stomach. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention can be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described supra. The compositions can be administered by the oral or nasal respiratory route for local or systemic effect. Compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can also be administered, orally or nasally, from devices which deliver the formulation in an appropriate manner.

IV. METHODS OF THE INVENTION

The telomerase inhibitor compounds (such as in pharmaceutical compositions) provided herein are useful for modulating disease states. In some embodiments, the cell proliferative disorder is associated with increased expression or activity of telomerase or cellular growth (such as neoplastic progenitor cells associated with the abnormal production of platelets in Essential Thrombocythemia (ET)), or both.

In some aspects, methods for alleviating at least one symptom associated with MPN in an individual in need thereof are provided herein. In some aspects, methods for alleviating at least one symptom associated with MDS in an individual in need thereof are provided herein. Also provided herein are methods for reducing neoplastic progenitor cell proliferation in patients with MPN or MDS, as well as methods for maintaining blood platelet concentrations and/or red blood cell concentrations and/or white blood cell conentrations at normal levels in individuals diagnosed with or suspected of having an MPN or an MDS.

Myeloproliferative neoplasms, or MPNs, are hematologic cancers that arise from malignant hematopoietic myeloid progenitor cells in the bone marrow, such as the precursor cells of red cells, platelets and granulocytes. Proliferation of malignant progenitor cells leads to an overproduction of any combination of white cells, red cells and/or platelets, depending on the disease. These overproduced cells may also be abnormal, leading to additional clinical complications. There are various types of chronic myeloproliferative disorders. Included in the MPN disease spectrum are Essential Thrombocythemia (ET), Polycythemia vera (PV), and chronic myelogenous leukemia (CML), myelofibrosis (MF), chronic neutrophilic leukemia, chronic eosinophilic leukemia and acute myelogenous leukemia (AML).

A myelodysplastic syndrome (MDS) is a group of symptoms that includes cancer of the blood and bone marrow. Myelodysplastic syndromes (MDS) includes diseases such as, refractory anemia, refractory anemia with excess blasts, refractory cytopenia with multilineage dysplasia, refractory cytopenia with unilineage dysplasia, and chronic myelomonocytic leukemia. The immature blood stem cells (blasts) do not become healthy red blood cells, white blood cells or platelets. The blast die in the bone marrow or soon after they travel to the blood. This leaves less room for healthy white cells, red cells and/or platelets to form in the bone marrow.

A. Essential Thrombocythemia

The megakaryocyte is a bone marrow cell responsible for the production of blood thrombocytes (platelets), which are necessary for normal blood clotting. Megakaryocytes normally account for 1 out of 10,000 bone marrow cells but can increase in number nearly 10-fold during the course of certain diseases.

Megakaryocytes are derived from hematopoietic stem cell precursor cells in the bone marrow. Once the cell has completed differentiation and become a mature megakaryocyte, it begins the process of producing platelets. While many cytokines are suspected to play a role in stimulating megakaryocytes to produce platelets, it is the cytokine thrombopoietin that induces the megakaryocyte to form small proto-platelet processes. Platelets are held within these internal membranes within the cytoplasm of megakaryocytes. Each of these proto-platelet processes can give rise to 2000-5000 new platelets upon breakup. Overall, ⅔ of these newly-produced platelets will remain in circulation while ⅓ will be sequestered by the spleen.

Essential Thrombocythemia (ET) is a chronic disorder associated with increased or abnormal production of blood platelets. Formation of platelets in ET occurs in a cytokine-independent fashion, with the megakaryocyte producing platelets in an unregulated manner. As platelets are involved in blood clotting, abnormal production can result in the inappropriate formation of blood clots or in bleeding, resulting in increased risk of gastrointestinal bleeding, heart attack and stroke.

Often, many patients with ET are asymptomatic; diagnosis typically occurs after blood counts as part of a routine check-up reveal a high platelet count. When ET symptoms are present, they may include fatigue, or may be related to small or large vessel disturbances or bleeding. Small vessel disturbances (often considered vasomotor in nature) can lead to: headache, vision disturbances or silent migraines, dizziness or lightheadedness, coldness or blueness of fingers or toes, or burning, redness, and pain in the hands and feet (www.mpnresearchfoundation.org/Essential-Thrombocythemia). Thrombotic complications can be quite serious, leading to: stroke, transient ischemic attack (TIA), heart attack, deep vein thrombosis or pulmonary embolus (blood clot in the lung). Bleeding can manifest as easy bruising, nosebleeds, heavy periods, gastrointestinal bleeding or blood in the urine (www.mpnresearchfoundation.org/Essential-Thrombocythemia). A small minority of people with ET may later develop acute leukemia or myelofibrosis, both of which can be life-threatening. Acute myelogenous leukemia is a type of blood and bone marrow cancer that progresses rapidly. Myelofibrosis is a progressive bone marrow disorder that results in bone marrow scarring, severe anemia, and enlargement of the liver and spleen.

According to the World Health Organization, diagnosis of ET requires that criteria A1 through A4 be met: (A1) a sustained platelet count of >450×10$^9$/L; (A2) bone marrow showing increased numbers of enlarged, mature megakaryocytes and no significant increase of left-shift of granulopoiesis or erythropoiesis; (A3) not meeting WHO criteria for polycythemia, primary myelofibrosis, chronic myeloid leukemia, myelodysplastic syndrome, or other myeloid neoplasm; and (A4) having an acquired mutation or clonal marker or no reactive cause for thrombocytosis (Swedlow, et al., (2008) *WHO Classification of Tumours of Haematopoietic and Lymphoid Tissues*, Lyon, IARC Press). When diagnosing ET, some clinicians use the British Committee for Standards in Haematology criteria (published in 2010), which are similar to the 2008 WHO criteria but differ in several significant respects (Beer, et al., (2010) *Blood* 117(5): 1472-1482).

Tests which may be done to diagnose ET include: (1) blood tests to exclude other causes of a high platelet count, including tests for iron deficiency and indicators of inflammation (other mimicking blood diseases are ruled out as well); (2) tests for JAK2 gene mutations (occurring in approximately 50% of cases) or MPL (occurring in up to 5% of cases); (3) bone marrow biopsies to look for classical signs of ET, including an increase in platelet precursors. Further information related to diagnosing ET can be found in U.S. Patent Application Publication No. 2006/0166221, which is incorporated by reference herein.

ET is generally treated through the use of: the modification of cardiovascular risk factors, antiplatelet therapy, and cytoreductive therapy (Beer, et al., *Blood* 117(5): 1472-1482; hereinafter (Beer et al., 2010). With respect to cardiovascular risk factors, patients are screened for the presence of hypertension, diabetes, smoking, hypercholesterolemia and obesity, and treated where indicated according to proper guidelines for those conditions (Beer et al., 2010). Antiplatelet therapy includes, but is not limited to: aspirin unless contraindicated and antiplatelet agents such as clopidogrel. ET patients may be stratified on the basis of thrombotic risk; high risk patients are over 60 years of age, have prior thrombotic events, or a platelet count greater than 1500×10$^9$/L; these high-risk patients will likely benefit from cytoreductive therapy (Beer et al., 2010).

Despite a possible increased risk of leukemic transformation when ET patients are treated with hydroxycarbamide (hydroxyurea), it remains the front-line therapy for most patients requiring treatment (Beer et al, 2010). Other treatments include but are not limited to interferon, anagrelide, pipobroman, busulphan, and irradiation with radioactive phosphorus.

Current drug therapy for ET is not curative and there is little evidence to suggest a favorable effect on survival. None of these current strategies addresses or directly targets either the malignant clonal cells responsible for the disease, the evolution of the disease, or the symptoms suffered by patients that affect quality of life. The goal of current therapy in ET is to prevent thrombohemorrhagic complications. Major progress in elucidating ET pathogenesis was made with the description, in 2005, of the JAK2 somatic mutation (V617F), which is present in 50-60% of ET patients (James, et al. (2005) *Nature* 434: 1144-1148; Kralovics, et al. (2005) *N Engl J Med* 352: 1779-90; Baxter, et al. (2005) *Lancet* 365: 1054-61; Levine, et al. (2005) *Cancer Cell* 7: 387-97). Besides presence and allele burden of JAK2/V617F mutation, baseline leukocytosis has been recently recognized as a new disease-related risk factor in ET (Ziakas P D. (2008) *Haematologica* 93: 1412-1414; Carobbio et al., (2007) *Blood* 109: 2310-2313). Evidence also indicates that leukocytosis has a prognostic significance and may be considered causative of vascular events (Barbui, et al., (2009) *Blood* 114: 759-63).

B. Polycythemia Vera

Patients with Polycythemia Vera (PV) have marked increases of red blood cell production. Treatment is directed at reducing the excessive numbers of red blood cells. PV can develop a phase late in their course that resembles primary myelofibrosis with cytopenias and marrow hypoplasia and fibrosis. The Janus Kinase 2 gene (JAK2) gene mutation on chromosome 9 which causes increased proliferation and survival of hematopoietic precursors in vitro has been identified in most patients with PV. Patients with PV have an increased risk of cardiovascular and thrombotic events and transformation to acute myelogenous leukemia or primary myelofibrosis. The treatment for PV includes intermittent chronic phlebotomy to maintain the hematocrit below 45% in men and 40% in women. Other possible treatments includes hydroxyurea, interferon-alpha, and low-dose aspirin.

C. Myelofibrosis

Myelofibrosis or MF, is a myeloproliferative neoplasm in the same spectrum of diseases as ET. Patients with MF often carry the JAK2 V617F mutation in their bone marrow. Occasionally ET evolves into MF. JAK2 inhibition is currently considered a standard of care for MF in countries where ruxolitinib (Jakafi®), a janus kinase inhibitor, is approved. There is no evidence that JAK2 inhibitors, such as Jakafi®, selectively inhibit proliferation of the leukemic clone responsible for the disease and thus, they may not be "disease modifying".

D. Acute Myelogenous Leukemia

Acute Myelogenous Leukemia (AML) is a cancer of the myeloid line of blood cells. AML is the most common acute leukemia affecting adults. Patients with AML have a rapid growth of abnormal white blood cells that accumulate in the bone marrow and interfere with the production of normal blood cells. Replacement of normal bone marrow with leukemic cells causes a drop in red blood cells, platelets, and normal white blood cells. The symptoms of AML include fatigue, shortness of breath, easy bruising and bleeding, and increased risk of infection. As an acute leukemia, AML progresses rapidly and is typically fatal within weeks or months if left untreated. The standard of care for AML is treatment with chemotherapy aimed at inducing a remission; patients may go on to receive a hematopoietic stem cell transplant.

E. Myelodysplastic Syndrome

A myelodysplastic syndrome (MDS) is a group of symptoms that includes cancer of the blood and bone marrow. The immature blood stem cells (blasts) do not become healthy red blood cells, white blood cells or platelets. The blast die in the bone marrow or soon after they travel to the blood. This leaves less room for healthy white cells, red cells and/or platelets to form in the bone marrow.

The myelodysplastic syndromes (MDS) are a collection of hematological medical conditions that involve ineffective production of the myeloid class of blood cells. Patients with MDS often develop severe anemia and require frequent blood transfusions. In some cases the disease worsens and the patient develops cytopenias (low blood counts) caused by progressive bone marrow failure. In some cases the disease transforms into acute myelogenous leukemia (AML). If the overall percentage of bone marrow myeloblasts rises over a particular cutoff (20% for WHO and 30% for FAB), then transformation to acute myelogenous leukemia (AML) is said to have occurred.

F. Methods for Treating MPN or MDS Using Telomerase Inhibitors

Provided herein are methods for reducing neoplastic progenitor cell proliferation and alleviating symptoms associated in individuals diagnosed with or thought to have MPN or MDS via administration of telomerase inhibitors (such as any of the telomerase inhibitors disclosed herein.

The methods can be practiced in an adjuvant setting. "Adjuvant setting" refers to a clinical setting in which an individual has had a history of a proliferative disease and generally (but not necessarily) been responsive to therapy, which includes, but is not limited to, surgery (such as surgical resection), radiotherapy, and chemotherapy. However, because of their history of the proliferative disease, these individuals are considered at risk of development of the disease. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated.

The methods provided herein can also be practiced in a "neoadjuvant setting," i.e., the method can be carried out before the primary/definitive therapy. In some embodiments, the individual has previously been treated. In some embodiments, the individual has not previously been treated. In some embodiments, the treatment is a first line therapy.

1. Methods for alleviating symptoms of Myeloproliferative Neoplasms and Myelodysplastic Syndroms In some aspects, the present invention is directed to methods for inhibiting the symptoms or conditions (disabilities, impairments) associated with Myeloproliferative Neoplasms as described in detail above. As such, it is not required that all effects of the condition be entirely prevented or reversed, although the effects of the presently disclosed methods likely extend to a significant therapeutic benefit for the patient. As such, a therapeutic benefit is not necessarily a complete prevention or cure for a particular condition resulting from Myeloproliferative Neoplasm, but rather, can encompass a result which includes reducing or preventing the symptoms that result from a cell proliferative disorder, reducing or preventing the occurrence of such symptoms (either quantitatively or qualitatively), reducing the severity of such symptoms or physiological effects thereof, and/or enhancing the recovery of the individual after experiencing Myeloproliferative Neoplasm symptoms.

In some aspects, the present invention is directed to methods for inhibiting the symptoms or conditions (disabilities, impairments) associated with Myelodysplastic Syndrome (MDS) as described in detail above. As such, it is not required that all effects of the condition be entirely prevented or reversed, although the effects of the presently disclosed methods likely extend to a significant therapeutic benefit for the patient. As such, a therapeutic benefit is not necessarily a complete prevention or cure for a particular condition resulting from Myelodysplastic Syndrome, but rather, can encompass a result which includes reducing or preventing the symptoms that result from a cell proliferative disorder, reducing or preventing the occurrence of such symptoms (either quantitatively or qualitatively), reducing the severity of such symptoms or physiological effects thereof, and/or enhancing the recovery of the individual after experiencing Myelodysplastic Syndrome symptoms.

As used herein, the phrase "alleviating at least one symptom associated with" a disorder, disease, or condition (such as MPN or MDS) denotes reversing, inhibiting the progress of, or preventing the disorder or condition to which such term applies, or reversing, inhibiting the progress of, or preventing one or more symptoms of the disorder or condition to which such term applies. Specifically, a composition of the present invention (such as any of the telomerase inhibitor compounds disclosed herein), when administered to an individual, can treat or prevent one or more of the symptoms or conditions associated with MPN or MDS and/or reduce or alleviate symptoms of or conditions associated with this disorder. As such, protecting an individual from the effects or symptoms resulting from MPN or MDS includes both preventing or reducing the occurrence and/or severity of the effects of the disorder and treating a patient in which the effects of the disorder are already occurring or beginning to occur. A beneficial effect can easily be assessed by one of ordinary skill in the art and/or by a trained clinician who is treating the patient. Preferably, there is a positive or beneficial difference in the severity or occurrence of at least one clinical or biological score, value, or measure used to evaluate such patients in those who have been treated with the methods of the present invention as compared to those that have not.

Accordingly, in some aspects, provided herein are methods for alleviating at least one symptom associated with MPN or MDS in an individual in need thereof, the method comprising: administering a clinically effective amount of a telomerase inhibitor to the individual, wherein administration of the telomerase inhibitor alleviates at least one symptom associated with MPN or MDS. In some embodiments, the symptom comprises headache, dizziness or lightheadedness, chest pain, weakness, fainting, vision changes, numbness or tingling of extremities, redness, throbbing or burning pain in extremities (erythromelalgia), enlarged spleen, nosebleeds, bruising, bleeding from mouth or gums, bloody stool, heart attack (myocardial infarction) or stroke. In some embodiments, the telomerase inhibitor comprises an oligonucleotide which can be complementary to the RNA component of telomerase and in some instances can be between 10-20 base pairs in length. In one embodiment, the oligonucleotide comprises the sequence TAGGGTTAGACAA (SEQ ID NO:12). In other embodiments, the oligonucleotide comprises N3'→P5' thiophosphoramidate internucleoside linkages. The oligonucleotide can also be conjugated to a lipid moiety on either its 5' or 3' end, optionally via a linker (such as a glycerol or amino glycerol linker). In some embodiments, the lipid moiety is a palmitoyl (C16) moiety. In yet another embodiment, the telomerase inhibitor is imetelstat. In some embodiments, administration of the telomerase inhibitor does not inhibit cytokine-dependent megakaryocyte growth. In other embodiments, administration of the telomerase inhibitor inhibits cytokine-independent megakaryocyte growth. In some embodiments, administration of the telomerase inhibitor inhibits CFU-mega. In yet other embodiments, inhibition of CFU-Mega is independent of reduction in JAK2 V617F allelic burden. In some embodiments, the individual can be resistant or intolerant to a prior non-telomerase inhibitor-based therapy (including, but not limited to hydroxyurea, anagrelide, or Interferon α-2B). In another embodiment, the individual is a human.

In some aspects, the effective amount of a telomerase inhibitor administered to the patient is 7.5 mg/kg to 9.3 mg/kg. In other aspects, the effective amount of a telomerase inhibitor is 9.5 mg/kg to 11.7 mg/kg. In some embodiments, the effective amount of a telomerase inhibitor includes at least about any of 6.5 mg/kg, 6.6 mg/kg, 6.7 mg/kg, 6.8 mg/kg, 6.9 mg/kg, 7 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9 mg/kg, 9.1 mg/kg, 9.2 mg/kg, 9.3 mg/kg, 9.5 mg/kg, 9.6 mg/kg, 9.7 mg/kg, 9.8 mg/kg, 9.9 mg/kg, 10 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, or 13 mg/kg. In some embodiments, the effective amount of a telomerase inhibitor administered to the individual is not 9.4 mg/kg.

In some aspects, the individual diagnosed with or thought to have MPN carries a V617F gain of function mutation in the Janus kinase 2 (JAK2) gene. Methods for determining whether an individual carries this mutation as well as determining allelic burden, are many and well known in the art (see, e.g., U.S. Patent Application Nos. 2009/0162849, 2007/0224598, and 2009/0162849, the disclosures of each of which are incorporated by reference. In some embodiments, administration of the telomerase inhibitor decreases the percentage of JAK2 V617F allelic burden in the individual.

2. Methods for Reducing Neoplastic Cell Proliferation

In another aspect, provided herein are methods for reducing neoplastic progenitor cell proliferation in an individual diagnosed with or suspected of having essential thrombocythemia, the method comprising: administering a clinically effective amount of a telomerase inhibitor to the individual, wherein administration of the telomerase inhibitor reduces neoplastic progenitor cell proliferation in the individual. In some embodiments, the telomerase inhibitor comprises an oligonucleotide which can be complementary to the RNA component of telomerase and in some instances can be between 10-20 base pairs in length. In one embodiment, the oligonucleotide comprises the sequence TAGGGTTAGACAA (SEQ ID NO:12). In other embodiments, the oligonucleotide comprises N3'→P5' thiophosphoramidate internucleoside linkages. The oligonucleotide can also be conjugated to a lipid moiety on either its 5' or 3' end, optionally via a linker (such as a glycerol or amino glycerol linker). In some embodiments, the lipid moiety is a palmitoyl (C16) moiety. In yet another embodiment, the telomerase inhibitor is imetelstat. In some embodiments, administration of the telomerase inhibitor does not inhibit cytokine-dependent megakaryocyte growth. In other embodiments, administration of the telomerase inhibitor inhibits cytokine-independent megakaryocyte growth. In some embodiments, administration of the telomerase inhibitor inhibits CFU-mega. In yet other embodiments, inhibition of CFU-Mega is independent of reduction in JAK2 V617F allelic burden. In some embodiments, the individual can be resistant or intolerant to a prior non-telomerase inhibitor-based therapy (including, but not limited to hydroxyurea, anagrelide, or Interferon α-2B). In another embodiment, the individual is a human.

In some aspects, reduced neoplastic progenitor cell proliferation results in platelet counts of less than any of about 600×10³/μL, 575×10³/μL, 550×10³/μL, 525×10³/μL, 500×10³/μL, 475×10³/μL, 450×10³/μL, 425×10³/μL, 400×10³/μL, 375×10³/μL, 350×10³/μL×10³/μL, 325×10³/μL, 300×10³/μL, 275×10³/μL, 250×10³/μL, 225×10³/μL, 200×10³/μL, 175×10³/μL, or 150×10³/μL in the blood of the individual, inclusive, including values in between these numbers. In other aspects, reduced neoplastic cell proliferation results in reduced platelet counts (such as any of the platelet counts described above) in the blood of the individual within any of about 24 weeks, 23 weeks, 22 weeks, 21 weeks, 20 weeks, 19 weeks, 18 weeks, 17 weeks, 16 weeks, 15 weeks, 14 weeks, 13 weeks, 12 weeks, 11 weeks, 10 weeks, 9 weeks, 8 weeks, 7 weeks, 6 weeks, 5 weeks, 4 weeks, 3 weeks, or 2 weeks or less following initiation of telomerase inhibitor administration.

In some aspects, the effective amount of a telomerase inhibitor is 7.5 mg/kg to 9.3 mg/kg. In other aspects, the effective amount of a telomerase inhibitor is 9.5 mg/kg to 11.7 mg/kg. In some embodiments, the effective amount of a telomerase inhibitor includes at least about any of 6.5 mg/kg, 6.6 mg/kg, 6.7 mg/kg, 6.8 mg/kg, 6.9 mg/kg, 7 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9 mg/kg, 9.1 mg/kg, 9.2 mg/kg, 9.3 mg/kg, 9.5 mg/kg, 9.6 mg/kg, 9.7 mg/kg, 9.8 mg/kg, 9.9 mg/kg, 10 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, or 13 mg/kg. In some embodiments, the effective amount of a telomerase inhibitor administered to the individual is not 9.4 mg/kg.

In some aspects, the individual diagnosed with or thought to have ET carries a V617F gain of function mutation in the Janus kinase 2 (JAK2) gene. In some embodiments, administration of the telomerase inhibitor decreases the percentage of JAK2 V617F allelic burden in the individual.

2. Methods for Maintaining Normal Levels of Circulating Platelets

In other aspects, provided herein for maintaining blood platelet counts of between less than about $400\times10^3/\mu L$ in the blood of an individual diagnosed with or suspected of having essential thrombocythemia, the method comprising: administering a clinically effective amount of a telomerase inhibitor to the individual, wherein administration of the telomerase inhibitor maintains blood platelet counts of less than about $400\times10^3/\mu L$ in the individual. In some embodiments, the telomerase inhibitor comprises an oligonucleotide which can be complementary to the RNA component of telomerase and in some instances can be between 10-20 base pairs in length. In one embodiment, the oligonucleotide comprises the sequence TAGGGTTAGACAA (SEQ ID NO:12). In other embodiments, the oligonucleotide comprises N3'→P5' thiophosphoramidate internucleoside linkages. The oligonucleotide can also be conjugated to a lipid moiety on either its 5' or 3' end, optionally via a linker (such as a glycerol or amino glycerol linker). In some embodiments, the lipid moiety is a palmitoyl (C16) moiety. In yet another embodiment, the telomerase inhibitor is imetelstat. In some embodiments, administration of the telomerase inhibitor does not inhibit cytokine-dependent megakaryocyte growth. In other embodiments, administration of the telomerase inhibitor inhibits cytokine-independent megakaryocyte growth. In some embodiments, administration of the telomerase inhibitor inhibits CFU-mega. In yet other embodiments, inhibition of CFU-Mega is independent of reduction in JAK2 V617F allelic burden. In some embodiments, the individual can be resistant or intolerant to a prior non-telomerase inhibitor-based therapy (including, but not limited to hydroxyurea, anagrelide, or Interferon α-2B). In another embodiment, the individual is a human.

In some aspects, administration of the telomerase inhibitors (such as any of the telomerase inhibitors described herein) maintains platelet counts at physiologically normal levels. In some embodiments, administration of the telomerase inhibitors maintains platelet counts of less than any of about $600\times10^3/\mu L$, $575\times10^3/\mu L$, $550\times10^3/\mu L$, $525\times10^3/\mu L$, $500\times10^3/\mu L$, $475\times10^3/\mu L$, $450\times10^3/\mu L$, $425\times10^3/\mu L$, $400\times10^3/\mu L$, $375\times10^3/\mu L$, $350\times10^3/\mu L\times10^3/\mu L$, $325\times10^3/\mu L$, $300\times10^3/\mu L$, $275\times10^3/\mu L$, $250\times10^3/\mu L$, $225\times10^3/\mu L$, $200\times10^3/\mu L$, $175\times10^3/\mu L$, or $150\times10^3/\mu L$ in the blood of the individual, inclusive, including values in between these numbers. In other aspects, administration of the telomerase inhibitors maintains platelet counts of between any of about $100\text{-}400\times10^3/\mu L$, $150\text{-}200\times10^3/\mu L$, $150\text{-}250\times10^3/\mu L$, $150\text{-}300\times10^3/\mu L$, $150\text{-}350\times10^3/\mu L$, $150\text{-}400\times10^3/\mu L$, $200\text{-}250\times10^3/\mu L$, $200\text{-}300\times10^3/\mu L$, $200\text{-}350\times10^3/\mu L$, $200\text{-}400\times10^3/\mu L$, $250\text{-}300\times10^3/\mu L$, $250\text{-}350\times10^3/\mu L$, $250\text{-}400\times10^3/\mu L$, $300\text{-}350\times10^3/\mu L$, $300\text{-}400\times10^3/\mu L$, or $350$ to $400\times10^3/\mu L$ in the blood of the individual.

In yet other aspects, maintaining blood platelet counts at physiologically normal levels requires administration of the telomerase inhibitor no more than once every day, every other day, every three days, every week, every 11 days, every two weeks, every three weeks, every month, every six weeks, every two months, or longer, inclusive, including time periods in between these.

In some aspects, the effective amount of a telomerase inhibitor is 7.5 mg/kg to 9.3 mg/kg. In other aspects, the effective amount of a telomerase inhibitor is 9.5 mg/kg to 11.7 mg/kg. In some embodiments, the effective amount of a telomerase inhibitor includes at least about any of 6.5 mg/kg, 6.6 mg/kg, 6.7 mg/kg, 6.8 mg/kg, 6.9 mg/kg, 7 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9 mg/kg, 9.1 mg/kg, 9.2 mg/kg, 9.3 mg/kg, 9.5 mg/kg, 9.6 mg/kg, 9.7 mg/kg, 9.8 mg/kg, 9.9 mg/kg, 10 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, or 13 mg/kg. In some embodiments, the effective amount of a telomerase inhibitor administered to the individual is not 9.4 mg/kg.

In some aspects, the individual diagnosed with or thought to have ET carries a V617F gain of function mutation in the Janus kinase 2 (JAK2) gene. In some embodiments, administration of the telomerase inhibitor decreases the percentage of JAK2 V617F allelic burden in the individual.

G. Administration of Telomerase Inhibitors

In some embodiments, the telomerase inhibitor (such as any of the telomerase inhibitor compounds disclosed herein) is administered in the form of an injection. The injection can comprise the compound in combination with an aqueous injectable excipient or carrier. Non-limiting examples of suitable aqueous injectable excipients or carriers are well known to persons of ordinary skill in the art, and they, and the methods of formulating the formulations, may be found in such standard references as Alfonso A R: *Remington's Pharmaceutical Sciences,* 17th ed., Mack Publishing Company, Easton Pa., 1985. Suitable aqueous injectable excipients or carriers include water, aqueous saline solution, aqueous dextrose solution, and the like, optionally containing dissolution enhancers such as 10% mannitol or other sugars, 10% glycine, or other amino acids. The composition can be injected subcutaneously, intraperitoneally, or intravenously.

In some embodiments, intravenous administration is used, and it can be continuous intravenous infusion over a period of a few minutes to an hour or more, such as around fifteen minutes. The amount administered can vary widely depending on the type of the telomerase inhibitor, size of a unit dosage, kind of excipients or carriers, and other factors well known to those of ordinary skill in the art. The telomerase inhibitor can comprise, for example, from about 0.001% to about 10% (w/w), from about 0.01% to about 1%, from about 0.1% to about 0.8%, or any range therein, with the remainder comprising the excipient(s) or carrier(s).

For oral administration, the telomerase inhibitor can take the form of, for example, tablets or capsules prepared by conventional means with pharmaceutically acceptable excipients or carriers such as binding agents; fillers; lubricants; disintegrants; or wetting agents. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations can also contain buffer salts, flavoring, and coloring as appropriate.

In some embodiments, the telomerase inhibitor can be administered by inhalation through an aerosol spray or a nebulizer that can include a suitable propellant such as, for example, dichlorodifluoromethane, trichlorofluoromethane, dichlorotetrafluoroethane, carbon dioxide, or a combination thereof. In one non-limiting example, a dosage unit for a pressurized aerosol can be delivered through a metering valve. In another embodiment, capsules and cartridges of gelatin, for example, can be used in an inhaler and can be formulated to contain a powderized mix of the compound with a suitable powder base such as, for example, starch or lactose.

In some embodiments, the amount of telomerase inhibitor administered to the individual is included in any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of a telomerase inhibitor in the effective amount administered to the individual (e.g., a unit dosage form) is in the range of about 5 mg to about 500 mg, such as about 30 mg to about 300 mg or about 50 mg to about 200 mg. In some embodiments, the concentration of the telomerase inhibitor administered to the individual is dilute (about 0.1 mg/ml) or concentrated (about 180 mg/ml), including for example any of about 0.1 to about 200 mg/ml, about 0.1 to about 180 mg/ml, about 0.1 to about 160 mg/ml, about 0.1 to about 140 mg/ml, about 0.1 to about 120 mg/ml, about 0.1 to about 100 mg/ml, about 0.1 to about 80 mg/ml, about 0.1 to about 60 mg/ml, about 0.1 to about 40 mg/ml, about 0.1 to about 20 mg/ml, about 0.1 to about 10 mg/ml about 2 to about 40 mg/ml, about 4 to about 35 mg/ml, about 6 to about 30 mg/ml, about 8 to about 25 mg/ml, about 10 to about 20 mg/ml, about 12 to about 15 mg/ml, or any of about 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2 mg/ml, 2.1 mg/ml, 2.2 mg/ml, 2.3 mg/ml, 2.4 mg/ml, or 2.5 mg/ml. In some embodiments, the concentration of the telomerase inhibitor is at least about any of 0.1 mg/ml, 0.2 mg/ml, 0.3 mg/ml, 0.4 mg/ml, 0.5 mg/ml, 1.3 mg/ml, 1.5 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 33.3 mg/ml, 34 mg/ml, 35 mg/ml, 36 mg/ml, 37 mg/ml, 38 mg/ml, 39 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, 150 mg/ml, 160 mg/ml, 170 mg/ml, 180 mg/ml, 190 mg/ml, 200 mg/ml, 210 mg/ml, 220 mg/ml, 230 mg/ml, 240 mg/ml, or 250 mg/ml.

Exemplary effective amounts of a telomerase inhibitor administered to the individual include, but are not limited to, at least about any of 25 mg/m$^2$, 30 mg/m$^2$, 50 mg/m$^2$, 60 mg/m$^2$, 75 mg/m$^2$, 80 mg/m$^2$, 90 mg/m$^2$, 100 mg/m$^2$, 120 mg/m$^2$, 125 mg/m$^2$, 150 mg/m$^2$, 160 mg/m$^2$, 175 mg/m$^2$, 180 mg/m$^2$, 200 mg/m$^2$, 210 mg/m$^2$, 220 mg/m$^2$, 250 mg/m$^2$, 260 mg/m$^2$, 300 mg/m$^2$, 350 mg/m$^2$, 400 mg/m$^2$, 500 mg/m$^2$, 540 mg/m$^2$, 750 mg/m$^2$, 1000 mg/m$^2$, or 1080 mg/m$^2$. In various embodiments, the amount of telomerase inhibitor administered to the individual includes less than about any of 350 mg/m$^2$, 300 mg/m$^2$, 250 mg/m$^2$, 200 mg/m$^2$, 150 mg/m$^2$, 120 mg/m$^2$, 100 mg/m$^2$, 90 mg/m$^2$, 50 mg/m$^2$, or 30 mg/m$^2$ of a telomerase inhibitor. In some embodiments, the amount of the telomerase inhibitor per administration is less than about any of 25 mg/m$^2$, 22 mg/m$^2$, 20 mg/m$^2$, 18 mg/m$^2$, 15 mg/m$^2$, 14 mg/m$^2$, 13 mg/m$^2$, 12 mg/m$^2$, 11 mg/m$^2$, 10 mg/m$^2$, 9 mg/m$^2$, 8 mg/m$^2$, 7 mg/m$^2$, 6 mg/m$^2$, 5 mg/m$^2$, 4 mg/m$^2$, 3 mg/m$^2$, 2 mg/m$^2$, or 1 mg/m$^2$. In some embodiments, the effective amount of a telomerase inhibitor administered to the individual is included in any of the following ranges: about 1 to about 5 mg/m$^2$, about 5 to about 10 mg/m$^2$, about 10 to about 25 mg/m$^2$, about 25 to about 50 mg/m$^2$, about 50 to about 75 mg/m$^2$, about 75 to about 100 mg/m$^2$, about 100 to about 125 mg/m$^2$, about 125 to about 150 mg/m$^2$, about 150 to about 175 mg/m$^2$, about 175 to about 200 mg/m$^2$, about 200 to about 225 mg/m$^2$, about 225 to about 250 mg/m$^2$, about 250 to about 300 mg/m$^2$, about 300 to about 350 mg/m$^2$, or about 350 to about 400 mg/m$^2$. In some embodiments, the effective amount of a telomerase inhibitor administered to the individual is about 5 to about 300 mg/m$^2$, such as about 20 to about 300 mg/m$^2$, about 50 to about 250 mg/m$^2$, about 100 to about 150 mg/m$^2$, about 120 mg/m$^2$, about 130 mg/m$^2$, or about 140 mg/m$^2$, or about 260 mg/m$^2$.

In some embodiments of any of the above aspects, the effective amount of a telomerase inhibitor administered to the individual includes at least about any of 1 mg/kg, 2.5 mg/kg, 3.5 mg/kg, 5 mg/kg, 6.5 mg/kg, 7.5 mg/kg, 9.4 mg/kg, 10 mg/kg, 15 mg/kg, or 20 mg/kg. In various embodiments, the effective amount of a telomerase inhibitor administered to the individual includes less than about any of 350 mg/kg, 300 mg/kg, 250 mg/kg, 200 mg/kg, 150 mg/kg, 100 mg/kg, 50 mg/kg, 30 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg of a telomerase inhibitor. In other embodiments of any of the above aspects, the effective amount of a telomerase inhibitor administered to the individual includes at least about any of 6.5 mg/kg, 6.6 mg/kg, 6.7 mg/kg, 6.8 mg/kg, 6.9 mg/kg, 7 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9 mg/kg, 9.1 mg/kg, 9.2 mg/kg, 9.3 mg/kg, 9.5 mg/kg, 9.6 mg/kg, 9.7 mg/kg, 9.8 mg/kg, 9.9 mg/kg, 10 mg/kg, 10.1 mg/kg, 10.2 mg/kg, 10.3 mg/kg, 10.4 mg/kg, 10.5 mg/kg, 10.6 mg/kg, 10.7 mg/kg, 10.8 mg/kg, 10.9 mg/kg, 11 mg/kg, 11.1 mg/kg, 11.2 mg/kg, 11.3 mg/kg, 11.4 mg/kg, 11.5 mg/kg, 11.6 mg/kg, 11.7 mg/kg, 11.8 mg/kg, 11.9 mg/kg, 12 mg/kg, 12.1 mg/kg, 12.2 mg/kg, 12.3 mg/kg, 12.4 mg/kg, 12.5 mg/kg, 12.6 mg/kg, 12.7 mg/kg, 12.8 mg/kg, 12.9 mg/kg, or 13 mg/kg. In some embodiments, the effective amount of a telomerase inhibitor administered to the individual is not 9.4 mg/kg. In other embodiments, the effective amount of a telomerase inhibitor administered to the individual is 7.5 mg/kg to 9.3 mg/kg. In yet other embodiments, the effective amount of a telomerase inhibitor is 9.5 mg/kg to 11.7 mg/kg.

Exemplary dosing frequencies for the pharmaceutical compositions (such as a pharmaceutical composition containing any of the telomerase inhibitors disclosed herein) include, but are not limited to, daily; every other day; twice per week; three times per week; weekly without break; weekly, three out of four weeks; once every three weeks; once every two weeks; weekly, two out of three weeks. In some embodiments, the pharmaceutical composition is administered about once every week, once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week, or three times daily, two times daily. In some embodiments, the intervals between each administration are less than about any of 6 months, 3 months, 1 month, 20 days, 15 days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week.

In other aspects, the pharmaceutical composition (such as a pharmaceutical composition containing any of the telomerase inhibitors disclosed herein) is administered to maintain blood platelet counts of between about $150 \times 10^3/\mu L$ to $400 \times 10^3/\mu L$ in the blood of an individual diagnosed with or suspected of having Essential Thrombocythemia. Under these conditions, the intervals between each administration can be weekly, every 2 weeks, every 3 weeks, or every 4 weeks or more. In some embodiments, the intervals for administration of the telomerase inhibitor can be decreased over time if platelet counts in the individual remain $<400 \times 10^3/\mu L$ in the blood of the individual. In some aspects, there is provided a method for determining the frequency of administration of the telomerase inhibitor for the treatment of ET comprising a) measuring an individual's blood platelet count by any means known in the art and b) administering the telomerase inhibitor if platelet counts in the individual are greater than $400 \times 10^3/\mu L$.

The administration of the pharmaceutical composition (such as a pharmaceutical composition containing any of the telomerase inhibitors disclosed herein) can be extended over an extended period of time (such as during maintenance therapy), such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months. In other embodiments, the composition is administered for the rest of the individual's lifetime.

EXAMPLES

Example 1

Preparation and Lipid Conjugation of Oligonucleotide N3→P5' Phosphoramidates (NP) or N3→P5' Thiophosphoramidates (NPS)

This example shows how to synthesize lipid conjugated Oligonucleotide N3→P5' Phosphoramidates (NP) or N3→P5' Thiophosphoramidates (NPS).
Materials and Methods
Starting Compounds
These compounds may be prepared as described, for example, in McCurdy et al., *Tetrahedron Letters* 38: 207-210 (1997) or Pongracz & Gryaznov, *Tetrahedron Letters* 49: 7661-7664 (1999). The starting 3'-amino nucleoside monomers may be prepared as described in Nelson et al., *J. Org. Chem.* 62: 7278-7287 (1997) or by the methods described in Gryaznov et al., US Application Publication No. 2006/0009636.

Lipid Attachment

A variety of synthetic approaches can be used to conjugate a lipid moiety L to the oligonucleotide, depending on the nature of the linkage selected; see, for example, Mishra et al., *Biochim. et Biophys. Acta* 1264: 229-237 (1995), Shea et al., *Nucleic Acids Res.* 18: 3777-3783 (1995), or Rump et al., *Bioconj. Chem.* 9: 341-349 (1995). Typically, conjugation is achieved through the use of a suitable functional group at an oligonucleotide terminus. For example, the 3'-amino group present at the 3'-terminus of the NP and NPS oligonucleotides can be reacted with carboxylic acids, acid chlorides, anhydrides and active esters, using suitable coupling catalysts, to form an amide linkage. Thiol groups are also suitable as functional groups (see Kupihar et al., *Bioorg. Med. Chem.* 9: 1241-1247 (2001)). Various amino- and thiol-functionalized modifiers of different chain lengths are commercially available for oligonucleotide synthesis.

Specific approaches for attaching lipid groups to a terminus of an NP or NPS oligonucleotide include those described in US Application Publication No. 2005/0113325, which is incorporated herein in its entirety by reference. In addition to the amide linkages noted above, for example, lipids may also be attached to the oligonucleotide chain using a phosphoramidite derivative of the lipid, to produce a phosphoramidate or thiophosphoramidate linkage connecting the lipid and the oligonucleotide. The free 3'-amino of the fully protected support-bound oligonucleotide may also be reacted with a suitable lipid aldehyde, followed by reduction with sodium cyanoborohydride, which produces an amine linkage.

For attachment of a lipid to the 5' terminus, as also described in US Application Publication No. 2005/0113325, the oligonucleotide can be synthesized using a modified, lipid-containing solid support. Reaction of 3'-amino-1,2-propanediol with a fatty acyl chloride (RC(O)Cl), followed by dimethoxytritylation of the primary alcohol and succinylation of the secondary alcohol, provides an intermediate which is then coupled, via the free succinyl carboxyl group, to the solid support. An example of a modified support is shown below, where S— represents a long chain alkyl amine CPG support, and R represents a lipid.

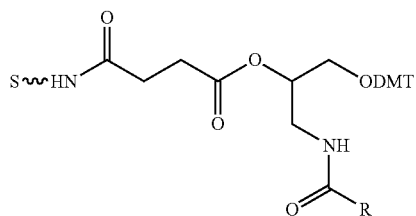

This procedure is followed by synthesis of the oligonucleotide in the 5' to 3' direction, as described, for example, in Pongracz & Gryaznov (1999), starting with deprotection and phosphitylation of the —ODMT group. This is effective to produce, for example, the following structure, after cleavage from the solid support:

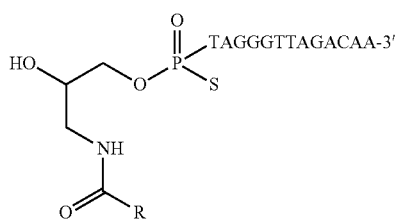

The structure above, when —R is —$(CH_2)_{14}CH_3$ (palmitoyl), is designated herein as GRN163L (Imetelstat) (SEQ ID NO:22).

FlashPlate™ Assay

This assay was carried out essentially as described in Asai et al., *Cancer Research* 63: 3931-3939 (2003). Briefly, the assay detects and/or measures telomerase activity by measuring the addition of TTAGGG telomeric repeats to a biotinylated telomerase substrate primer. The biotinylated products are captures on streptavidin-coated microtiter plates, and an oligonucleotide probe complementary to 3.5 telomere repeats, labeled with 33P, is used for measuring telomerase products. Unbound probe is removed by washing, and the amount of probe annealing to the captured telomerase products is determined by scintillation counting.

Example 2

Imetelstat Inhibits the Spontaneous Growth of CFU-Meg In Vitro From Essential Thrombocythemia Patients and Myelofivrosis Patients but not from Healthy Individuals This example demonstrates a dose-dependent suppression of colony-forming unit megakaryocytes (CFU-Mega) by imetelstat in patients with essential thrombocythemia or Myelofibrosis independent of the JAKV617F mutational status or cytoreductive therapy, suggesting a specificity of imetelstat for malignant megakaryocytic cells.

Materials and Methods

For determining imetelstat effect on megakaryocyte growth and differentiation the following methods were used: (1) cord blood (CB) cells were enriched for CD34+ expressing cells using a negative cell separation system; (2) cells were incubated with imetelstat (1-15 μM) in serum-free liquid medium, StemSpan® SFEM, containing a cytokine formulation designed for the development of megakaryocyte progenitor cells; (3) cord blood cells were cultured for a total of 17 days; and (4) at various time points, cells were enumerated and assessed by flow cytometry for differentiation markers (CD41) and for telomerase activity by TRAP assay.

For determining CFU-Mega dose response curves, mononuclear cells (MNC) from 3 healthy individuals and from 11 ET patients and one myelfibrotic (MF) patient (determined using WHO 2009 criteria) were isolated from peripheral blood and suspended in IMDM or plated into collagen ±cytokines (TPO, IL3, IL6, SCF, EPO) and treated with 0, 0.1, 1 and 10 μM imetelstat or a mismatch control, and incubated for several hours (cell suspensions) or 10-12 days (collagen plus 5% $CO_2$) at 37° C. Megakaryocytes were stained and the number of CFU-Meg was scored. The dose-response analysis utilized a 4 parameter log-logistic model for $Log_{10}$ (colony count) by dose. Telomerase activity was measured in MNC by TRAP assay.

Results

FIGS. 1A and 1B show imetelstat does not inhibit megakaryocyte growth or differentiation in healthy donors.

Table 1 shows spontaneous growth of CFU-Mega and inhibition by imetelstat.

TABLE 1

CFU-Mega % in Patients with Essential Thrombocythemia

| Patient ID | 0 μM [%] | 0.1 μM [%] ± SD [%] | 1 μM [%] ± SD [%] | 10 μM [%] ± SD [%] |
|---|---|---|---|---|
| 1* | 100 | 138 ± 5.7 | 119 ± 3.8 | 46 ± 1.9 |
| 2* | 100 | 106 ± 4.3 | 48 ± 4.3 | 39 ± 4.3 |
| 3* | 100 | 104 ± 5.7 | 96 ± 11.3 | 44 ± 5.7 |
| 4* | 100 | 77 ± — | 3 ± — | 14 ± — |
| 5 | 100 | 138 ± 33.7 | 81 ± 23.6 | 52 ± 6.7 |
| 6 | 100 | 117 ± 4.9 | 52 ± — | 45 ± 45.6 |
| 7 | 100 | 33 ± 5.9 | 29 ± 0.0 | 13 ± 2.9 |
| 8* | 100 | 141 ± 9.6 | 49 ± 13.4 | 14 ± — |
| 9* | 100 | 80 ± 14.1 | 40 ± 7.1 | 40 ± — |
| 10 | 100 | 130 ± 1.6 | 66 ± 8.1 | 3 ± 0.4 |
| 11* | 100 | 114 ± 0 | 95 ± 34.4 | 49 ± 7.6 |
| N = 11 | 100 | 107 ± 8.6 | 79 ± 11.8 | 33 ± 9.4 |

*JAK2 V617F-positive

Table 2 shows cytokine-stimulated growth of CFU-Mega and no inhibition by imetelstat.

TABLE 2

CFU-Meg (%) in Healthy Individuals

| Donor ID | 0 μM [%] C+ | 0.1 μM [%] ± SD [%] C+ | 1 μM [%] ± SD [%] C+ | 10 μM [%] ± SD [%] C+ |
|---|---|---|---|---|
| 1 | 100 | 93 ± 10 | 96 ± 5 | 86 ± 10 |
| 2 | 100 | 109 ± 58 | 109 ± 51 | 173 ± 13 |
| 3 | 100 | 111 ± 47 | 122 ± 20 | 78 ± 16 |
| N = 3 | 100 | 104 ± 38 | 109 ± 25 | 112 ± 13 |

Figure 7:
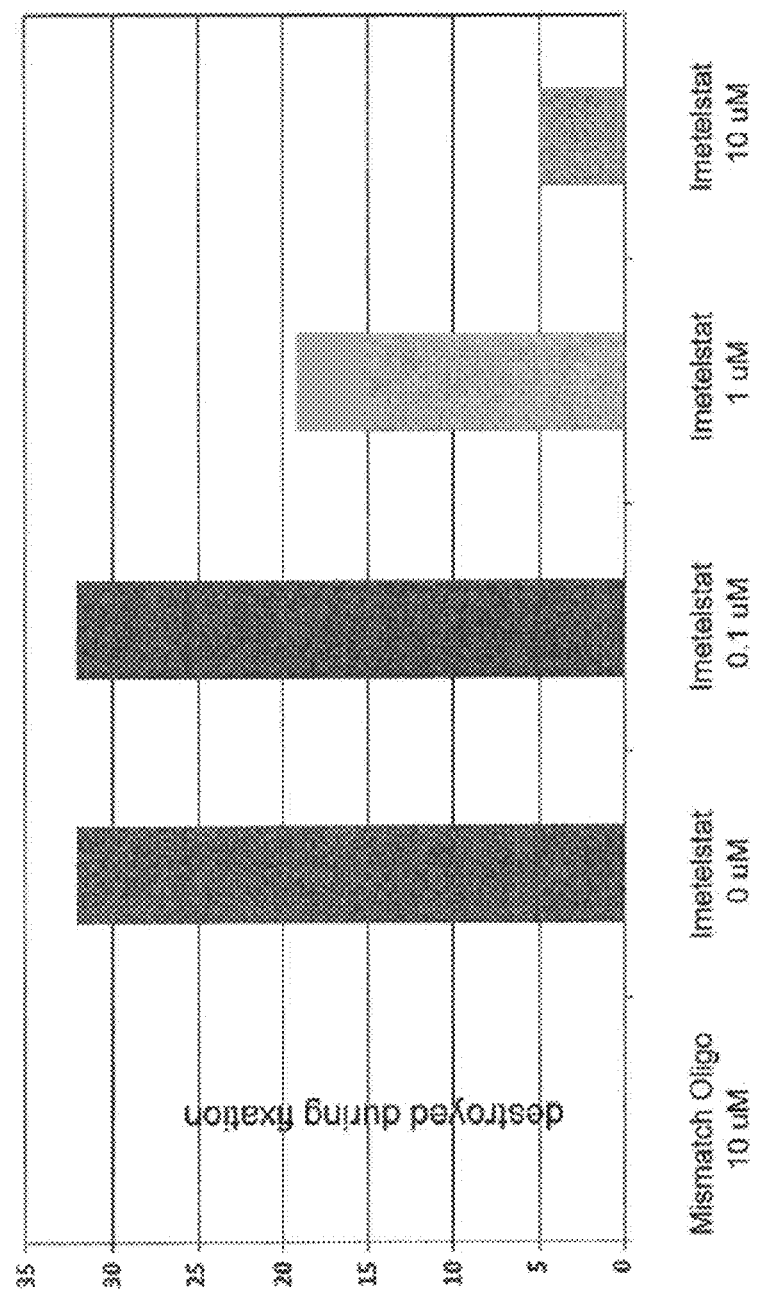
FIG. 7 depicts imetelstat effects on megakaryocyte growth and differentiation from a patient with primary myelofibrosis.

FIG. 7 shows that imetelstat inhibits megakaryocyte growth or differentiation in a myelofibrosis patient.

Figure 2:
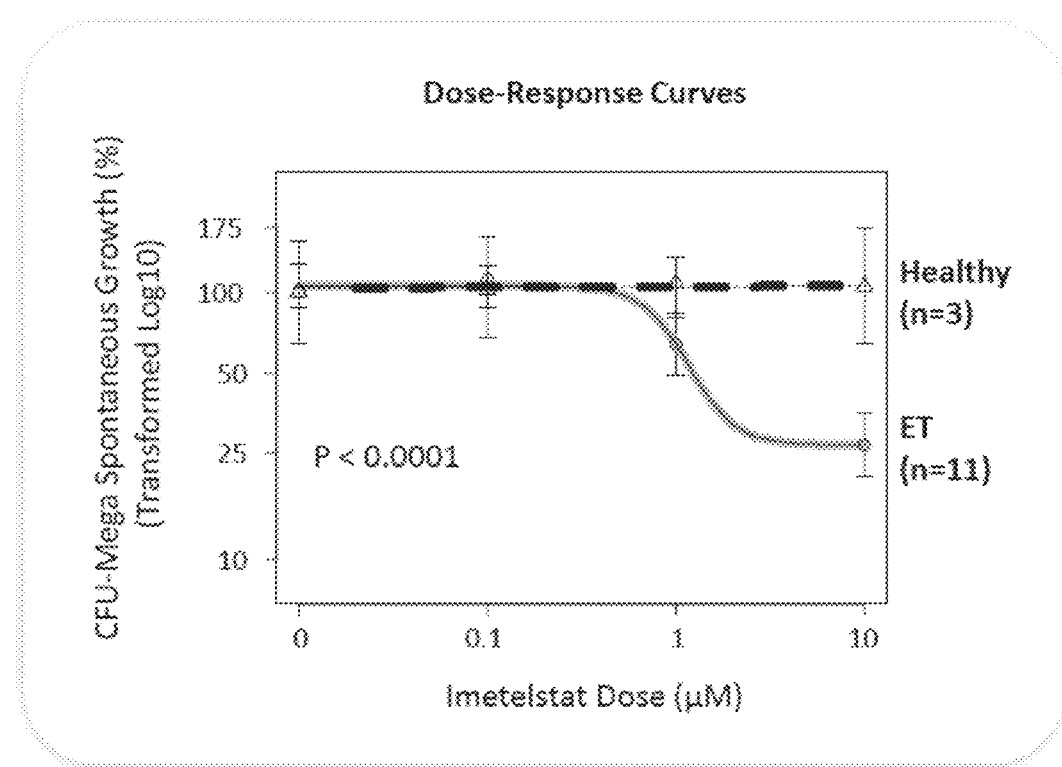
FIG. 2 depicts colony-forming unit megakaryocytes (CFU-Mega) dose response curves.

The dose response curves in FIG. 2 and the results in FIG. 7 show imetelstat reduces neoplastic progenitor proliferation. CFU-Mega from peripheral blood indicates imetelstat inhibits neoplastic (spontaneous) megakaryocyte growth from patients with ET and MF, but does not inhibit normal (cytokine-dependent) megakaryocyte growth from healthy individuals. This dose-dependent suppression of CFU-Mega formation by imetelstat in patients with ET is independent of the JAKV617F mutational status or cytoreductive therapy.

Example 3

Phase II Trial to Evaluate the Activity of Imetelstat (GRN163L) in Patients with Essential Thrombocythemia Who Require Cytoreduction and have Failed or are Intolerant to Previous Therapy, or Who Refuse Standard Therapy (Phase II Imetelstat ET Study)

This example demonstrates imetelstat rapidly induces and maintains substantial hematologic and molecular responses in patients with essential thrombocythemia (ET) who were refractory to or intolerant to prior therapy.

Materials and Methods

Clinical Trial Design

Patients with ET who had failed or were intolerant to at least one prior therapy (or who had refused standard therapy) and required cytoreduction were induced with 7.5-11.7 mg/kg Imetelstat given as a 2 hour intravenous infusion weekly, with doses titrated to platelet response. When a platelet count of 250-300×10³/μL was achieved, maintenance dosing with imetelstat was then initiated with doses increased or decreased based upon platelet response and toxicity, with a goal of less frequent dosing in the maintenance phase.

ET-specific patient inclusion criteria were: (1) a confirmed diagnosis of ET by World Health Organization (WHO) criteria; (2) the patient with ET required cytoreduction and had failed or was intolerant to at least one prior therapy (or had refused standard therapy). Laboratory criteria (within 14 days of first study drug administration) were: (1) platelets >600,000/μL; (2) ANC≥1500/μL; (3) hemoglobin ≥10 g/dL.

General criteria for all patients were: (1) willing and able to sign an informed consent form; (2) male or female, aged 18 years or older; (3) ECOG performance status of 0-2. Laboratory criteria for all patients were (within 14 days of first study drug administration): (1) INR (or PT) and aPTT<1.5× the upper limit of normal (ULN); (2) serum creatine ≤2 mg/dL; (3) serum bilirubin <2.0 mg/dL (patients with Gilbert's syndrome: serum bilirubin <3×ULN); (4) AST (SGOT) and ALT (SGPT)≤2.5×ULN; (5) alkaline phosphatase <2.5 ULN; (6) any clinically significant toxicity from previous cancer treatments and/or major surgery must have recovered to Grade 0-1 prior to initiation of study treatment.

Patients who met any of the following criteria were excluded from screening and study entry: (1) women who were pregnant or breast feeding; (2) prior stem cell transplantation; (3) investigational therapy within 4 weeks prior to first study drug administration; (4) clinically significant cardiovascular disease or condition including: (a) uncontrolled congestive heart failure (CHF); (b) need for antiarrhythmic therapy for a ventricular arrhythmia; (c) clinically significant severe conduction disturbance per the Investigator's discretion; (d) ongoing angina pectoris requiring therapy; (e) New York Heart Association (NYHA) Class II, III, or IV cardiovascular disease; (f) known positive serology for human immunodeficiency virus (HIV); (g) serious co-morbid medical conditions, including active or chronically recurrent bleeding, clinically relevant active infection, cirrhosis, and chronic obstructive or chronic restrictive pulmonary disease per the Investigator's discretion; or (h) any other severe, acute, or chronic medical or psychiatric condition, laboratory abnormality, or difficulty complying with protocol requirements that may increase the risk associated with study participation or study drug administration or may interfere with the interpretation of study results and, in the judgment of the Investigator, would make the patient inappropriate for the study.

The primary outcome measure was the best overall hematologic response rate (RR) (complete response (CR)+partial response (PR)). The time frame was from time of the first dose (cycle 1 day 1) through the end of the study (12 months after last participant is dosed).

The secondary endpoint objectives were to determine the duration of hematologic response, to determine the molecular response (JAK2 V617F/MPL W515$^{mt}$ patients), and to examine safety and tolerability by monitoring number of patients with hematological toxicities, non-heme Grade 3 and 4 adverse events (AEs), and hemorrhagic events. The time frame was from the time of the first dose (cycle 1 day 1) through the end of the study (12 months after the last participant was dosed). The exploratory objective was CFU-Mega spontaneous growth (selected sites only).

Table 3 sets forth the response definitions for the study. European Leukemia Net Response Criteria were adapted from Barosi et al., *Blood* (2009). Heme response was counted as the latest of the 4 weeks.

TABLE 3

Response Definitions

| | Definition |
|---|---|
| Hematologic Response Grade | |
| Complete Response (CR) | Normalization of platelets (≤400 × 10³/μL) maintained for at least 4 consecutive weeks, in the absence of thromboembolic events. |
| Partial Response (PR) | Platelets (≤600 × 10³/μL) or a 50% reduction in platelets maintained for at least 4 consecutive weeks, in the absence of thromboembolic events. |
| Molecular Response Grade | |
| Complete Response (CR) | Reduction of any specific molecular abnormality to undetectable levels. |
| Partial Response (PR)* *Applies only to patients with a baseline value of mutant allele burden ≥10% | 1) A reduction of ≥50% from baseline value in patients with <50% mutant allele burden at baseline OR 2) A reduction of ≥25% from baseline value in patients with >50% mutant allele burden at baseline. |
| No Response (NR) | Any response that does not satisfy complete or partial response. |

Patient demographics are provided in Table 4 below.

TABLE 4

Patient Demographics

| Characteristic Median (Range) | Total (N = 14) |
|---|---|
| Age | 59.5 years (21-83) |
| Years Since Initial Diagnosis | 5.8 (0.3-24.9) |
| Median Baseline Platelet Count | 787.5 × 10³/μL (521-1359) |
| Median Baseline WBC Count | 6.6 × 10³/μL (3.0-14.6) |
| Pts with JAK2 V617F | 7 (50%) |
| Pts with MPL515$^{mt}$ | 2 (14.3%) |
| More than one prior therapy (anagrelide +/− IFN)* *All 14 patients received prior hydroxyurea (6 resistant, 8 intolerant) | 9 (64%) |
| Resistant to at least one prior therapy | 7 (50%) |
| Intolerant of or refused at least one prior therapy | 11 (71%) |

Results

Figure 3:
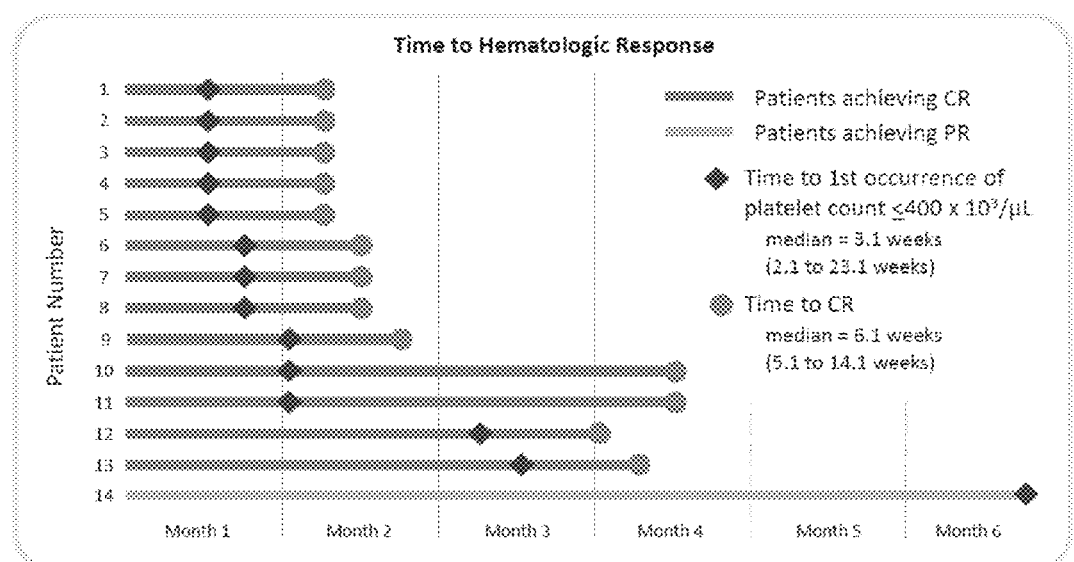
FIG. 3 depicts results for the primary study endpoint (hematologic response) from the Phase II Trial to Evaluate the Activity of Imetelstat (GRN163L) in Patients with Essential Thrombocythemia Who Require Cytoreduction and Have Failed or Are Intolerant to Previous Therapy, or Who Refuse Standard Therapy (Phase II Imetelstat ET Study). CR, complete response; PR, partial response. The time to the first occurrence of platelet count $\leq 400 \times 10^3/\mu L$ is represented by diamond shapes, while the time to complete response is indicated by circles.

FIG. 3 shows a 100% overall hematologic response was achieved in all 14 patients with ET who had failed or were intolerant to conventional therapies. A complete response was achieved in 13 of 14 patients (92.9%) and a partial response in 1 of 14 patients (7.1%). All patients who attained a hematologic CR remain on treatment. The data indicated that the time to a first occurrence of platelet count ≤400×10³/μL (marked for each patient with a diamond) had a median value of 3.1 weeks (2.1 to 23.1 weeks), while the time to complete response had a median value of 6.1 weeks (5.1 to 14.1 weeks) (FIG. 3).

Data on dosing frequency for the 13 patients who had a hematologic complete response and began maintenance therapy are provided in Table 5 below. Maintenance dosing frequency generally decreased with time (range was weekly to Q7 weeks) with the majority (84.6% or 11/14) of patients receiving imetelstat every 2 weeks or less frequently (based on the median). 85.7% of patients (6/7) who were eligible to remain on therapy after 1 year have continued maintenance therapy.

TABLE 5

Dosing Frequency in Maintenance

| Median frequency of therapy | N = 13 |
|---|---|
| Weekly | 2 (15.4%) |
| Every 2 weeks | 3 (23.1%) |
| Every 3 weeks | 2 (15.4%) |
| >Every 3 weeks | 6 (46.1%) |

Figure 4:
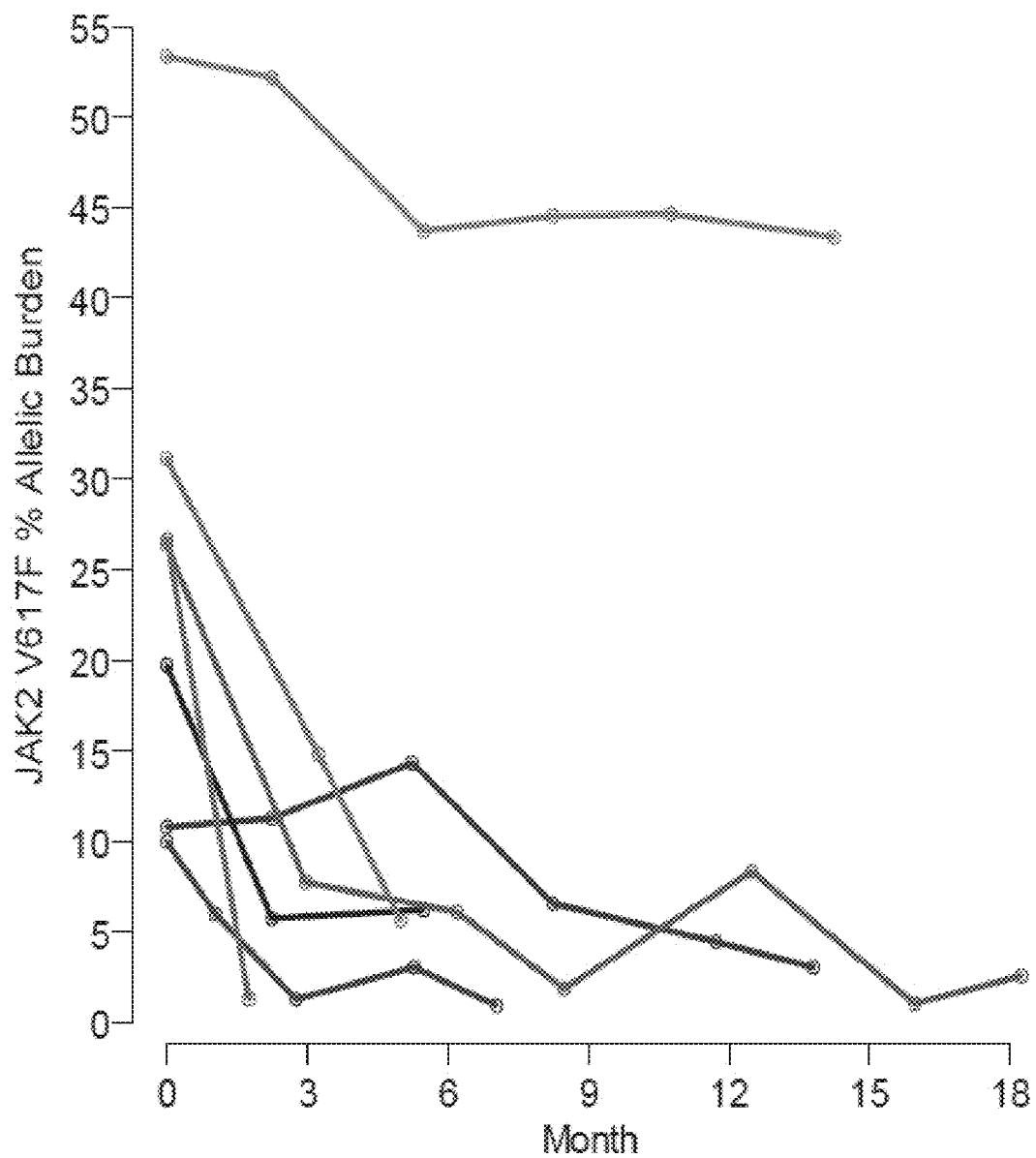
FIGS. 4A and 4B depict the Phase II Imetelstat ET Study results for the secondary study endpoint (JAK2 V617F Allelic Burden). PR, partial response.
Figure 4:
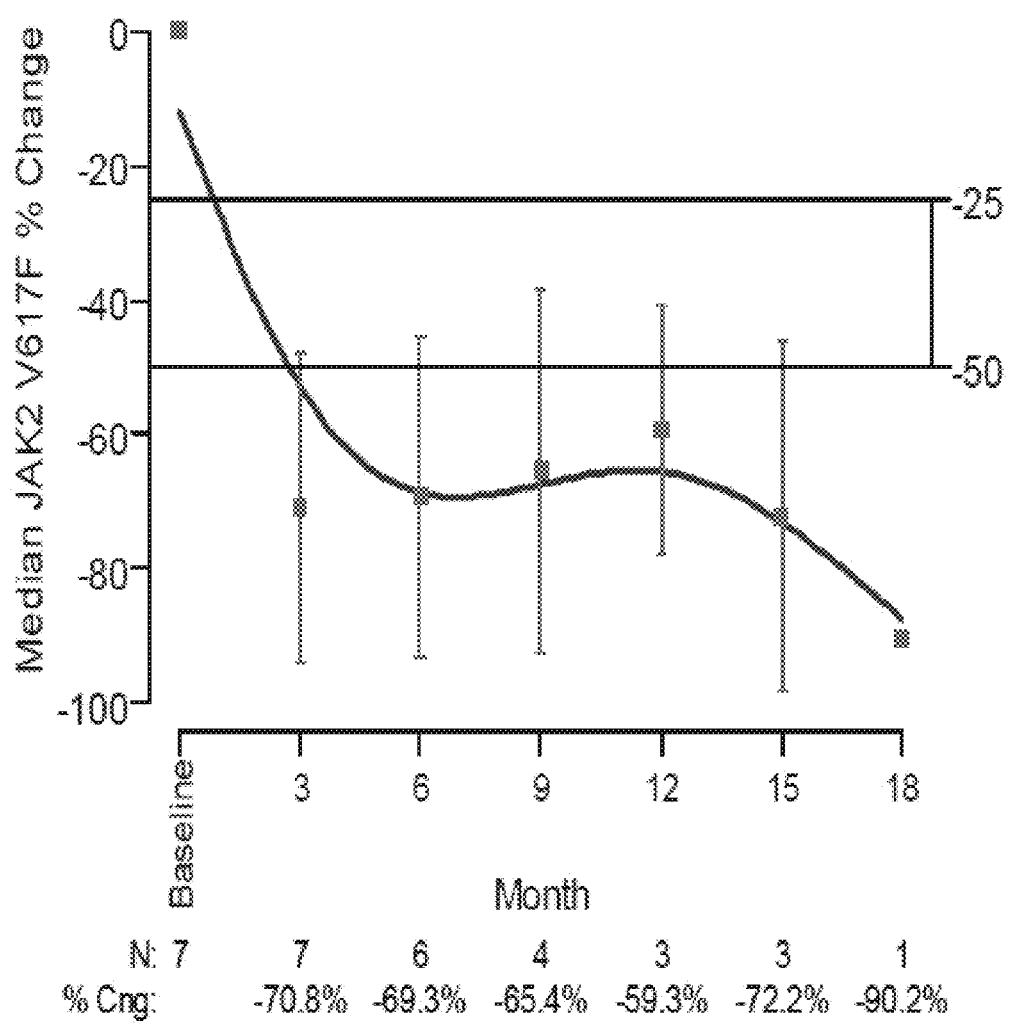

As shown in FIG. 4A, the % JAK2 V617F allelic burden decreased over time in all patients, while FIG. 4B shows molecular responses (PR) were reached in 6/7 (85.7%) patients tested with JAPK2 V617F within a 3-6 month range.

Table 6 shows the results regarding the exploratory endpoint (CFU-Mega). Reduced spontaneous growth of CFU-Mega ex-vivo was demonstrated in the two patients tested (93% and 96% reduction from baseline, respectively), confirming prior ex vivo data.

TABLE 6

Results for Exploratory Endpoint - CFU-Mega

| Patient # | Baseline | 1 month |
|---|---|---|
| 4 | 22.7 | 1.7 |
| 8 | 8.0 | 0.3 |

Figure 5:
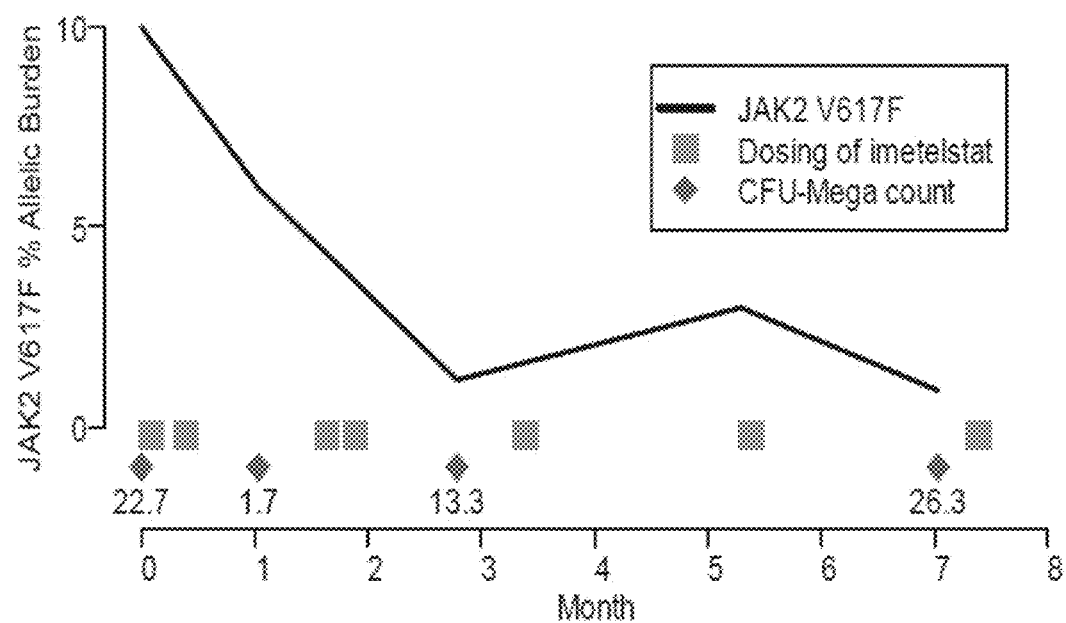
FIG. 5 depicts the Phase II Imetelstat ET Study results for the exploratory endpoint (CFU-Mega).

FIG. 5 shows spontaneous growth of CFU-Mega did not correspond with the reduction in JAK2 allelic burden in one patient (patient #4).

The data suggest that imetelstat has a relatively selective inhibitory effect on the growth of the neoplastic clone(s) which drive myeloproliferative neoplasms (MPNs) such as essential thrombocythemia and has the potential to modify the underlying biology of the disease.

Table 7 shows the clinically significant frequent non-hematologic adverse events.

TABLE 7

Safety - Clinically Significant Frequent Non-Hematologic Adverse Events

| Frequent Non-Hematologic Adverse Events | All Grades (N = 14) | Grade 3 (N = 14) |
|---|---|---|
| GI Events (Nausea/Diarrhea/Constipation) | 14 (100%) | 0 |
| Infections | 12 (85.7%) | 1* (7.1%) |
| Fatigue | 9 (64.3%) | 1 (7.1%) |
| Musculoskeletal Disorders | 9 (64.3%) | 0 |
| Bleeding Events | 8 (57.1%) | 1** (7.1%) |
| Headache | 7 (50%) | 1 (7.1%) |
| Cough | 7 (50%) | 0 |
| Decreased Appetite | 7 (50%) | 0 |
| Dizziness | 6 (42.9%) | |
| Infusion Reactions | 4 (28.6%) | 1*** (7.1%) |

One Grade 4 adverse event: imetelstat unrelated neck fracture. No Grade 5 adverse events and no thromboembolic events were reported.
*Grade 3 cellulitis/wound infection
**Grade 3 post-operative hemorrhagic anemia
***Grade 3 syncope; patient remains on treatment Table 8 shows the laboratory abnormalities:

TABLE 8

Safety - Laboratory Abnormalities

| Laboratory Parameter | All Grades (N = 14) | Grade 3 (N = 14) | Grade 4 |
|---|---|---|---|
| ALT/AST (change from baseline grade) | 13 (92.9%) | 2 (14.3%) | 0 |
| Neutropenia | 11 (78.6%) | 4 (28.6%) | 2 (14.3%) |
| Anemia (change from baseline grade) | 9 (64.3%) | 1 (7.1%)* | 0 |
| Thrombocytopenia | 6 (42.9%) | 0 | 0 |

No cases of febrile neutropenia reported.
*Post-operative hemorrhagic anemia

Example 4

A Pilot Open Label Study of the Efficacy and Safety of Imetelstat (GRN163L) in Patients with DIPSS plus Intermediate-2 or High Risk Primary Myelofibrosis (PMF), Post-polycythemia Vera Myelofibrosis (Post-PV MF) or Post-Essential Thrombocythemia Myelofibrosis (Post-ET MF)

Materials and Methods

Clinical Trial Design

Patients with DIPSS plus Intermediate-2 or High Risk Primary Myelofibrosis (PMF), post-polycythemia Vera Myelofibrosis (post-PV MF) or Post-Essential Thrombocythemia Myelofibrosis (post-ET MF) who were not on active standard therapy were induced with 9.4 mg/kg Imetelstat given as a 2 hour intravenous infusion once every 21 days. Patients may receive treatment for a maximum of 9 cycles. Patients may continue therapy beyond 9 cycles.

PMF-specific patient inclusion criteria were: (1) a confirmed diagnosis of ET by World Health Organization (WHO) criteria; (2) megakaryocyte proliferation with atypia accompanied by either reticulin and/or collagen fibrosis or (4) not meeting WHO criteria for CML, PV, MDS or other myeloid neoplasm or (5) no evidence of reactive marrow fibrosis.

Post-PV MF-specific patient inclusion criteria were: (1) a confirmed diagnosis of PV by World Health Organization (WHO) criteria; (2) bone marrow fibrosis grade 2-3 (on a 0-3 scale) or grade 3-4 (on a 0-4 scale) and (3) two or more of (a) anemia or sustained loss of requirement for phlebotomy in the absence of cytoreductive therapy or (b) leukoerythroblastic peripheral blood picture or (c) increasing splenomegaly defined as either an increase in palpable splenomegaly of ≥5 cm or the appearance of a newly palpable splenomegaly or (d) development of ≥1 of the three constitutional symptoms: 0.10% weight loss in 6 months, night sweats, unexplained fever (0.37.5° C.).

Post-ET MF-specific patient inclusion criteria were: (1) a confirmed diagnosis of ET by World Health Organization (WHO) criteria; (2) bone marrow fibrosis grade 2-3 (on a 0-3 scale) or grade 3-4 (on a 0-4 scale) and (3) two or more of (a) anemia and a ≥2 g/dL decrease from baseline hemoglobin level or (b) leukoerythroblastic peripheral blood picture or (c) increasing splenomegaly defined as either an increase in palpable splenomegaly of ≥5 cm or the appearance of a newly palpable splenomegaly or (d) increased castate dehydrogenase or (e) development of ≥1 of the three constitutional symptoms: 0.10% weight loss in 6 months, night sweats, unexplained fever (0.37.5° C.).

General criteria for all patients were: (1) willing and able to sign an informed consent form; (2) male or female, aged 18 years or older; (3) ECOG performance status of 0-2. Laboratory criteria for all patients were (within 14 days of first study drug administration): (1 AST (SGOT) and ALT (SGPT)≤2.5× ULN; (2) creatine ≤3 mg/dL; (3) absolute neutrophil count ≥1000/μL; (4) platelet count ≥50,000/μL; (5) absence of active treatment with systemic anticoagulation and a baseline PT and aPTT that does not exceed 1.5×UNL.

Patients who met any of the following criteria were excluded from screening and study entry: (1) women who were pregnant or breast feeding; (2) any chemotherapy immunomodulatory drug therapy, immunosuppressive therapy, corticosteroids 0.10 mg/day prednisone or equivalent, growth factor treatment or JAK inhibitor therapy ≤14 days prior to registration; (4) subjects with another active malignancy. (5) known positive status for HIV (6) any unresolved toxicity greater for equal to Grade 2 from previous anticancer therapy (6) incomplete recovery from any prior surgical procedures (7) presence of acute active infection requiring antibiotics (8) uncontrolled intercurrent illness or any concurrent condition that would jeopardize the safety of the patient or compliance with the protocol.

The primary outcome measure was the best overall response rate (RR) (clinical improvement (CI) or complete response (CR) or partial response (PR)). The time frame was from time of the first dose (cycle 1 day 1) through the first 9 cycles of treatment.

The secondary endpoint objectives were to determine the (a) adverse events, (b) the spleen response: defined as either a minimum 50% reduction in palpable splenomegaly of a spleen that is at least 10 cm at baseline or a spleen that is palpable at more than 5 cm ab baseline (c) transfusion-independence: where transfusion dependency is defined as a history of at least 2 units of red blood cell transfusions in the last month for a hemoglobin level of less than 85 g/L that was not associated with clinically overt bleeding. The time frame was from the time of the first dose (cycle 1 day 1) through the end of the study. The exploratory objective was (a) bone marrow histology assessment of reversal of bone marrow fibrosis to a lower grade and (b) portion of patients with baseline leukocytosis and thrombocytosis who achieve at least 50% reduction in their counts at the end of cycles 3, 6 and 9.

Table 3 sets forth the response definitions for the study. Intentional Working Group (IWG) consensus criteria for treatment response in myelofibrosis with myeloid metaplasia were used.

TABLE 3

Response Definitions

| | Definition |
|---|---|
| Complete Remission (CR) | Complete resolution of disease-related symptoms and signs including palpable hepatosplenomegaly Peripheral blood count remission defined as hemoglobin level at least 110 g/L, platelet count at least 100 × 10$^9$/L, and absolute neutrophil count at least 1.0 × 10$^9$/L. In addition, all 3 blood counts should be no higher than the upper normal limit Normal leukocyte differential including disappearance of nucleated red blood cells, blasts and immature myeloid cells in the peripheral smear, in the absence of splenectomy Bone marrow histologic remission defined as the presence of age-adjusted normocellularity, no more than 5% myeloblasts and an osteomyelofibrosis grade no higher than 1. |
| Partial Remission (PR) | requires all of the above criteria for CR except the requirement for bone marrow histologic remission. However, a repeat bone marrow biopsy is required in the assessment of PR and may or may not show favorable changes that do |

TABLE 3-continued

Response Definitions

| | Definition |
|---|---|
| | not however fullfil criteria for CR. |
| Clinical Improvement (CI) | Requires one of the following in the absence of both disease progression and CR/PR assignment<br>1. a minimum 20 g/L increase in hemoglobin level or becoming transfusion independent (applicable only for patients with baseline pretransfusion hemoglobin level of 100 g/L<br>2. either minimum 50% reduction in palpable splenomegaly of a spleen that is at least 10 cm at baseline or a spleen that is palpable at more than 5 cm at baseline becomes not palpable<br>3. a minimum 100% increase in platelet count and an absolute platelet count of at least 50,000 × 10$^9$/L (applicable only for patients with baseline platelet count below 50 × 10$^9$/L<br>4. a minimum 100% increase in ANC and an ANC of at least 0.5 × 10$^9$/L(applicable only for patients with baseline neutrophil count below 1 × 10$^9$/L). |
| Progressive Disease (PD)) | Requires one of the following:<br>1. Progressive splenomegaly that is defined by the appearance of a previously absent splenomegaly that is palpable at greater than 5 cm below the left costal margin or a minimum 100% increase in palpable distance for baseline splenomegaly of 5-10 cm or a minimum 50% increase in palpable distance for baseline splenomegaly of greater than 10 cm<br>2. Leukemic transformation confirmed by a bone marrow blast count of at least 20%<br>3. An increase in peripheral blood blast percentage of at least 20% that lasts for at least 8 weeks. |
| Stable Disease | None of the above |
| Relapse | Loss of CR, PR or CI |

Results

Clinical benefit has been observed in patients enrolled in the study.

Example 5

Imetelstat Inhibits the Spontaneous Growth of CD34+ Cells In Vitro From Acute Myeloid Leukemia Patients but not from Healthy Individuals This example demonstrates a dose-dependent suppression of CD34+ cells by imetelstat in patients with acute myeloid leukemia, suggesting a specificity of imetelstat for malignant CD34+ cells.

Materials and Methods

For determining imetelstat effect the following methods were used: (1) bone marrow cells were incubated with imetelstat (0.1-10 μM) in a colony forming assay and in liquid culture for a total of 14 days and at various time points, cells were enumerated and assessed.

For determining CFU dose response curves, bone marrow cells from 4 healthy individuals or from 5 AML patients were isolated from peripheral blood plated and treated with 0, 0.1, 1 and 10 μM imetelstat or a mismatch control. The CFU-GM (colony forming unit-granulocyte, macrophage) and BFU-E (burst-forming unit-erythroid) were stained and the number of CFU-GM and BFU-E were scored.

Results

Imetelstat did not reduce CFU from the bone marrow of a healthy donor in a 14 day CFU assay.

Reduction of CFU of bone marrow cells from an AML patient was observed upon treatment with imetelstat in a 14 day CFU assay.

Imtelstat reduced cell growth from bone marrow cells of newly diagnosed AML patients in a 14 day liquid culture assay.

Figure 6:
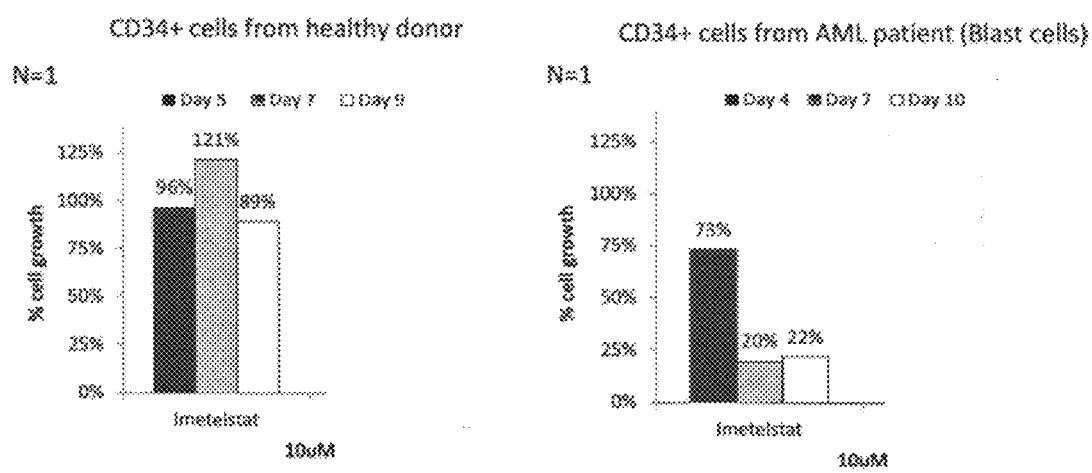
FIG. 6 depicts the percentage of cell growth in culture after in vitro treatment with Imetelstat of CD34+ cells obtained from a healthy donor and CD34+ cells from an AML patient at day 5, day 7 and day 9.

Imetelstat reduced the growth of CD34+ cells derived from an AML patient's bone marrow cells but not from a normal patient's bone marrow. FIG. 6 depict the percentage of cell growth in culture after in vitro treatment with Imetelstat of CD34+ cells obtained from a healthy donor and CD34+ cells from an AML patient at day 5, day 7 and day 9.

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation. All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for alleviating at least one symptom associated with myelofibrosis (MF) or myelodysplastic syndrome in an individual in need thereof, the method comprising: administering a clinically effective amount of a telomerase inhibitor to the individual, wherein administration of the telomerase inhibitor alleviates at least one symptom associated with myelofibrosis (MF) or myelodysplastic syndrome.

2. The method of claim 1, wherein the symptom comprises headache, dizziness or lightheadedness, chest pain, weakness, fainting, vision changes, numbness or tingling of extremities, redness, throbbing or burning pain in extremities (erythromelalgia), enlarged spleen, nosebleeds, bruising, bleeding from mouth or gums, bloody stool, or stroke.

3. The method of claim 1 wherein the at least one symptom is associated with myelofibrosis (MF).

4. The method of claim 1 wherein the myelodysplastic syndrome is selected from the group consisting of refractory anemia, refractory anemia with excess blasts, refractory cytopenia with multilineage dysplasia, refractory cytopenia with unilineage dysplasia, and chronic myelomonocytic leukemia (CMML).

5. The method of claim 4 wherein the myelodysplastic syndrome (MDS) is chronic myelomonocytic leukemia (CMML).

6. A method for reducing neoplastic progenitor cell proliferation in an individual diagnosed with or suspected of having myelofibrosis (MF) or myelodysplastic syndrome, the method comprising: administering a clinically effective amount of a telomerase inhibitor to the individual, wherein administration of the telomerase inhibitor reduces neoplastic progenitor cell proliferation in the individual.

7. The method of claim 6 wherein the individual is diagnosed with or suspected of having myelofibrosis (MF).

8. The method of claim 6 wherein the myelodysplastic syndrome is selected from the group consisting of refractory anemia, refractory anemia with excess blasts, refractory cytopenia with multilineage dysplasia, refractory cytopenia with unilineage dysplasia, and chronic myelomonocytic leukemia (CMML).

9. The method of claim 6, wherein the individual is resistant or intolerant to a prior non-telomerase inhibitor-based therapy.

10. A method for reducing bone marrow fibrosis in an individual diagnosed with or suspected of having myelofibrosis (MF) or myelodysplastic syndrome, the method comprising: administering a clinically effective amount of a telomerase inhibitor to the individual, wherein administration of the telomerase inhibitor reduces bone marrow fibrosis in the individual.

11. The method of claim 6, wherein the telomerase inhibitor comprises an oligonucleotide.

12. The method of claim 11, wherein the oligonucleotide is complementary to the RNA component of telomerase.

13. The method of claim 11, wherein the oligonucleotide is 10-20 bases in length.

14. The method of claim 11, wherein the oligonucleotide comprises the sequence TAGGGTTAGACAA (SEQ ID NO:12).

15. The method of claim 11, wherein the oligonucleotide comprises at least one N3'→P5' thiophosphoramidate internucleoside linkage.

16. The method of claim 15, wherein the oligonucleotide comprises N3'→P5' thiophosphoramidate internucleoside linkages.

17. The method of claim 11, wherein the oligonucleotide further comprises a lipid moiety linked to the 5' and/or 3' end of the oligonucleotide.

18. The method of claim 17, wherein the lipid moiety is linked to the 5' and/or 3' end of the oligonucleotide via a linker.

19. The method of claim 18, wherein the linker is a glycerol or aminoglycerol linker.

20. The method of claim 18, wherein the lipid moiety is a palmitoyl (C16) moiety.

21. The method of claim 6, wherein the telomerase inhibitor is imetelstat.

22. The method of claim 6, wherein the telomerase inhibitor is administered with a pharmaceutically acceptable excipient.

23. The method of claim 6, wherein the telomerase inhibitor is formulated for oral, intravenous, subcutaneous, intramuscular, topical, intraperitoneal, intranasal, inhalation, or intraocular administration.

24. The method of claim 6, wherein administration of the therapeutically effective amount of the telomerase inhibitor comprises contacting one or more neoplastic progenitor cells with the telomerase inhibitor.

25. The method of claim 21, wherein the effective amount of a telomerase inhibitor is 7.5 mg/kg to 9.3 mg/kg.

26. The method of claim 21, wherein the effective amount of a telomerase inhibitor is 9.5 mg/kg to 11.7 mg/kg.

27. The method of claim 6, wherein administration of the telomerase inhibitor does not inhibit cytokine-dependent megakaryocyte growth.

28. The method of claim 6, wherein the individual carries a V617F gain of function mutation in the Janus kinase 2 (JAK2) gene.

29. The method of claim 28, wherein administration of the telomerase inhibitor decreases the percentage of JAK2 V617F allelic burden in the individual.

30. The method of claim 6, wherein administration of the telomerase inhibitor inhibits cytokine-independent megakaryocyte growth.

31. The method of claim 6, wherein administration of the telomerase inhibitor inhibits CFU-mega.

32. The method of claim 31, wherein inhibition of CFU-Mega is independent of reduction in JAK2 allelic burden.

33. The method of claim 1, wherein the telomerase inhibitor comprises an oligonucleotide with the following characteristics:
   (a) 10-20 bases in length;
   (b) complementary to the RNA component of telomerase; and
   (c) comprises at least one N3'→P5' thiophosphoramidate internucleoside linkage.

34. The method of claim 33, wherein the telomerase inhibitor further comprises a lipid moiety linked to the 5' and/or 3' end of the oligonucleotide.

35. The method of claim 34, wherein the lipid moiety is linked to the 5' and/or 3' end of the oligonucleotide via a linker.

36. The method of claim 35, wherein the oligonucleotide comprises a lipid moiety linked to the 5' end of the oligonucleotide via an aminoglycerol linker.

37. The method of claim 36, wherein the lipid moiety is a palmitoyl (C16) moiety.

38. The method of claim 37, wherein the lipid moiety is linked to the 5' end of the oligonucleotide via an aminoglycerol linker and a 5'-thiophosphate group.

39. The method of claim 33, wherein the oligonucleotide comprises the sequence TAGGGTTAGACAA (SEQ ID NO:12).

40. The method of claim 6, wherein the telomerase inhibitor comprises an oligonucleotide with the following characteristics:
   (a) 10-20 bases in length;
   (b) complementary to the RNA component of telomerase; and
   (c) comprises at least one N3'→P5' thiophosphoramidate internucleoside linkage.

41. The method of claim 40, wherein the telomerase inhibitor further comprises a lipid moiety linked to the 5' and/or 3' end of the oligonucleotide.

42. The method of claim 41, wherein the lipid moiety is linked to the 5' and/or 3' end of the oligonucleotide via a linker.

43. The method of claim 42, wherein the oligonucleotide comprises a lipid moiety linked to the 5' end of the oligonucleotide via an aminoglycerol linker.

44. The method of claim 43, wherein the lipid moiety is a palmitoyl (C16) moiety.

45. The method of claim 44, wherein the lipid moiety is linked to the 5' end of the oligonucleotide via an aminoglycerol linker and a 5'-thiophosphate group.

46. The method of claim 40, wherein the oligonucleotide comprises the sequence TAGGGTTAGACAA (SEQ ID NO:12).

47. The method of claim 10, wherein the telomerase inhibitor comprises an oligonucleotide with the following characteristics:
   (a) 10-20 bases in length;
   (b) complementary to the RNA component of telomerase; and
   (c) comprises at least one N3'→P5' thiophosphoramidate internucleoside linkage.

48. The method of claim 47, wherein the telomerase inhibitor further comprises a lipid moiety linked to the 5' and/or 3' end of the oligonucleotide.

49. The method of claim 48, wherein the lipid moiety is linked to the 5' and/or 3' end of the oligonucleotide via a linker.

50. The method of claim 49, wherein the oligonucleotide comprises a lipid moiety linked to the 5' end of the oligonucleotide via an aminoglycerol linker.

51. The method of claim 50, wherein the lipid moiety is a palmitoyl (C16) moiety.

52. The method of claim 51, wherein the lipid moiety is linked to the 5' end of the oligonucleotide via an aminoglycerol linker and a 5'-thiophosphate group.

53. The method of claim 47, wherein the oligonucleotide comprises the sequence TAGGGTTAGACAA (SEQ ID NO:12).

* * * * *